United States Patent
Gaumond et al.

(10) Patent No.: US 6,379,311 B1
(45) Date of Patent: Apr. 30, 2002

(54) BREATHING DISORDER PRESCREENING DEVICE AND METHOD

(75) Inventors: Roger Paul Gaumond, State Collete, PA (US); Seok-Hyon Jo, Escondido, CA (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

(21) Appl. No.: 09/677,315

(22) Filed: Sep. 29, 2000

Related U.S. Application Data

(63) Continuation-in-part of application No. 09/307,678, filed on May 10, 1999, now Pat. No. 6,183,423.
(60) Provisional application No. 60/085,466, filed on May 14, 1998.

(51) Int. Cl.[7] .................................................. A61B 5/08

(52) U.S. Cl. ........................ 600/529; 600/532; 600/538

(58) Field of Search ............................... 600/529, 531, 600/532, 533, 538, 530

(56) References Cited

U.S. PATENT DOCUMENTS

| | | |
|---|---|---|
| 5,666,960 A | 9/1997 | Fredberg et al. |
| 5,746,699 A | 5/1998 | Fredberg et al. |

OTHER PUBLICATIONS

Wu et al., "Upper Airway Collapsibility in Normal Subjects and Patients with Obstructive Sleep Apnea," Apr. 1998, pp. 1–26.
Sales literature of SensorMedics for EccoVision product.
Douglas et al, "Pharyngeal Size in Snorers, and Patients with Obstructive Sleep Apnea," New England Journal of Medicine, vol. 315, No. 21, Nov. 20, 1986, pp. 1327–1331.
Clerk et al., "Load Detection in Subjects with Sleep–induced Upper Airway Obstruction," Am. J. Respir, Crit Care Med., vol. 149, Nov. 20, 1992, pp. 727–730.
Gleadhill et al., "Upper Airway Collapsibility in Snorers and in Patients with Obstructive Hypopnea and Apnea," Am. Rev. Respir. Dis., vol. 143, 1991, pp. 1300–1303.
Gleeson et al., "The Influence of Increasing Ventilatory Effort on Arousal from Sleep," Am. Rev. Respir. Dis., vol. 142, 1990, pp. 295–300.
Greenberg et al., "Depressed Ventilatory Load Compensation in Sleep Apnea," Am. Rev. Respir. Dis., vol. 148, 1993, pp. 1608–1615.
Hendricks et al., "Upper Airway Dilating Muscle Hyperactivity During Non–Rapid Eye Movement Sleep in English Bulldogs," Am. Rev. Respir. Dis., vol. 148, 1993, pp. 185–194.
Hoffstein et al., "Lung Volume Dependence of Pharyngeal Cross–Sectional Area in Patients with Obstructive Sleep Apnea," Am. Rev. Respir. Dis., vol. 130, 1984, pp. 175–178.
Horner et al., "Sites and Sizes of Fat Deposits Around the Pharynx in Obese Patients with Obstructive Sleep Apnoea and Weight Matched Controls," Eur. Respir. J., 1989, pp. 613–922.

(List continued on next page.)

*Primary Examiner*—Kevin Shaver
*Assistant Examiner*—Navin Natnithithadha
(74) *Attorney, Agent, or Firm*—Michael W. Haas

(57) ABSTRACT

An apparatus for diagnosing a breathing disorder of a patient that includes a first sensing system that determines a dimension, such as cross-sectional area, of a portion of the patient's airway and an internal load determination system that determines an internal load on the airway. A processing system receives the output from the first sensing system and the internal load determination system and determines a compliance curve that corresponds to a relationship between the measured dimension and a plurality of internal loads on the patient's airway. The processing system also determines at least one characteristic associated with the compliance curve. This characteristic is indicative of a likelihood that the patient suffers from a breathing disorder.

18 Claims, 10 Drawing Sheets

OTHER PUBLICATIONS

Hudgel, "Variable Site of Airway Narrowing Among Obstructive Sleep Apnea Patients," Amer. Physiological Society, 1986, pp. 1403–1409.

Kim et al., "Effect of Inspiration Pressure Support on the Arousal Response to CO2 in Sleeping Dogs," Journal of Appied Physiology, vol. 79, No. 5, 1995, pp. 1419–1425.

Kimoff et al., "Mechanisms of Apnea Termination in Obstructive Sleep Apnea," Am. J. Fespir. Crit. Care Med., vol. 149, 1994, pp. 707–714.

Kimoff et al., "Effect of Inspiratory Muscle Unloading on Arousal Responses to CO2 and Hypoxia in Sleeping Dogs," Amer. Physiological Society, 1993, pp. 1325–1336.

Kimura et al., "The Effect of Hypoxic Depression on Genioglossal Muscle Activity in Healthy Subjects and Obstructive Sleep Apnea Patients," American Sleep Disorders Assn. and Sleep Reseasrch Society, vol. 16, 1993, pp. S135–S136.

Lopata et al., "Mass Loading, Sleep Apnea, and the Pathogenesis of Obesity Hypoventilation," Am. Rev. Respir. Dis., vol. 126, 1982, pp. 640–645.

Louis et al., "Pulmonary Airway Area by the Two–Microphone Acoustic Reflection Method," American Physiological Society, 1994, pp. 2234–2240.

Mezzanotte et al., "Waking Genioglossal Electromyogram in Sleep Apnea Patients versus Normal Controls (a Neuromuscular Compensatory Mechanism)," The Journal of Clinical Investigations, Inc., vol. 89, 1991, pp. 1571–1579.

Morrison et al., "Pharyngeal Narrowing and Closing Pressure in Patients with Obstructive Sleep Apnea," Am. Rev. Respir. Dis., vol. 148, 1993, pp. 606–611.

Rubinstein et al., "Lung Volume–Related Changes in the Pharyngeal Area of Obese Females With and Without Obstructive Sleep Apnoea," Eur. Respir. J., vol. 2, 1989, pp. 344–351.

Scardella et al., "Strength and Endurance Characteristics of the Normal Human Genioglossus," Am. Rev. Respir. Dis., vol. 148, 1993, pp. 181–184.

Schwartz et al., "Effect of Weight Loss on Upper Airway Collapsibility in Obstructive Sleep Apnea," Am. Rev. Respir. Dis., vol. 144, 1991, pp. 494–498.

Schwartz et al., "Induction of Upper Airway Occlusion in Sleeping Individuals with Subatmospheric Nasal Pressure," Americal Physiological Society, 1988, pp. 535–542.

Shelton et al., "Pharyngeal Fat in Obstructive Sleep Apnea," Am. Rev. Respir. Dis., vol. 148, 1993, pp. 462–466.

Shepard et al., "Localization of Upper Airway Collapse during Sleep in Patients with Obstructive Sleep Apnea," Am. Rev. Respir. Dis., vol. 141, 1990, pp. 1350–1355.

Stauffer et al., "Pharyngeal Size and Resistance in Obstructive Sleep Apnea," Am. Rev. Respir. Dis., vol. 136, 1987, pp. 623–627.

Smith et al., "Upper Airway Pressure–Flow Relationships in Obstructive Sleep Apnea," American Physiological Society, 1988, pp. 789–795.

Tangel et al., "Influence of Sleep on Tensor Palatini EMG and Upper Airway Resistance in Normal Men," American Physiological Society, 1991, pp. 2574–2581.

Voorhees et al., "Magnetically Induced Contraction of the Inspiratory Muscles in Dog,"Journal of Clinical Engineering, vol. 15, No. 5, Sep.–Oct., 1990, pp. 407–409.

Wheatley et al., "Influence of Sleep on Genioglossus Muscle Activation by Negative Pressure in Normal Men," Am. Rev. Respir. Dis., vol. 148, 1993, pp. 597–605.

Wheatley et al., "The Influence of Sleep on Pharyngeal Reflexes," Americal Sleep Disorders Association and Sleep Research Society, vol. 16, 1993, pp. S87–S89.

Wiegand et al., "Collapsibility of the Human Upper Airway During Normal Sleep," Journal of Applied Physiology, vol. 66, 1989, pp. 1800–1808.

Eccovision Acoustic Pharyngometry System Operator Manual, 1996, pp. (1–1)–(D–2).

BREATHING DISORDER PRESCREENING DEVICE AND METHOD

CROSS REFERENCE TO RELATED APPLICATIONS

This is a Continuation-In-Part (CIP) of prior U.S. patent application Ser. No. 09/307,678, filed May 10, 1999, now U.S. Pat. No. 6,183,423, which claims priority under 35 U.S.C. § 119(e) from U.S. provisional patent application No. 60/085,466, filed May 14, 1998.

BACKGROUND OF THE INVENTION

1. Field of the Invention

The present invention pertains to an apparatus and method for diagnosing a breathing disorder, and, in particular, to an apparatus that determines a dimension of a portion of a patient's airway, such as a cross-sectional area of the airway, for each of a plurality of internal loads imposed on the patient's airway and, from this information, assesses the likelihood that the patient suffers from a breathing disorder. The present invention also pertains to a method of diagnosing the likelihood that a patient suffers from a breathing disorder using such an apparatus.

2. Description of the Related Art

Obstructive sleep apnea ("OSA") is a condition in which sleep is repeatedly interrupted by an inability to breathe due to an obstructed upper airway segment. Those afflicted with OSA experience sleep fragmentation and complete or nearly complete cessation of ventilation intermittently and repeatedly during sleep with potentially severe degrees of oxyhemoglobin desaturation. These symptoms may translate clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during wakefulness, as well as during sleep, and continuous reduced arterial oxygen tension. Hypersomnolent sleep apnea patients may be at risk for excessive mortality from these factors as well as by an elevated risk for accidents while driving and/or operating potentially dangerous equipment.

Using conventional techniques, OSA cannot be readily diagnosed in a physician's office or in a hospital during a short visit. Instead, present methods for diagnosing OSA rely on polysomnography to measure the patient's apnea/hypopnea index ("AHI"), which takes place over a period of several hours while the patient is asleep, typically during an overnight sleep monitoring session. This conventional diagnostic technique commonly takes place in a sleep laboratory, which is in a hospital or a clinic. Portable polysomnography devices exist that enable the sleep monitoring session to take place at the patient's home. However, home monitoring requires that the patient place the monitoring system and sensors on himself or herself and operate the polysomnography monitoring device, which may result in erroneous or inefficient placement of the sensors and/or improper use of the monitor. A caregiver may assist the patient at home in placing the sensors and operating the monitoring system. However, this is costly and time consuming.

It can be appreciated that the conventional overnight procedure for diagnosing OSA, whether in a sleep lab or at home, is time consuming for both the patient and the technician monitoring the patient. This diagnostic technique is also generally inconvenient and may be unsettling to the patient because it typically requires that the patient stay in the hospital or the clinical setting overnight and that the patient wear a myriad of sensors while trying to sleep. The likelihood that the monitoring session will be unsettling is especially true for children and patient's with an elevated level of apprehension concerning medical facilities, such as patient's with infirm mental abilities.

Conventional OSA diagnostic procedures also requires a significant amount of processing of complex physiological data by a trained technician, which, again, is time-consuming and costly. Thus, conventional diagnostic procedures, because of their overly burdensome and perhaps onerous techniques, as well as exorbitant expense, are not suitable as a prescreening tool to determine if there is even a likelihood that the patient may suffer from OSA. Rather, conventional diagnostic techniques are best used if it is already determined that there is a likelihood that the patient suffers from OSA. In which case, the conventional techniques can be more appropriately targeted to functions such as determining an appropriate therapy to treat the patient. A practical and reliable prescreening technique would identify patients who are not likely to suffer from OSA so that they can avoid the relatively time consuming and burdensome overnight diagnostic session and also identify those patients who are likely suffers from OSA so that additional diagnosis (if necessary) and treatment can be obtained.

Indications for sleep apnea are generally a patient's complaint or the complaints of a spouse or a sleep partner of daytime somnolence and/or frequent awakening episodes while sleeping or trying to sleep. These indicators, however, are highly subjective and may be attributable to other factors. In addition, some OSA sufferers, including children and patients afflicted with Down's Syndrome, have difficulty clearly communicating the nature of their problem with sleep interruption. Thus, these indicators, whether elucidated from the patient via a written questionnaire or orally, are not entirely reliable as a prescreening indication of OSA. Also, physical indicators, such as increased lung residual volume or subsequent cardiovascular complications, are also generally not strong indicators of OSA.

SUMMARY OF THE INVENTION

Accordingly, it is an object of the present invention to provide an apparatus for diagnosing, at least for prescreening purposes, whether a patient is likely to suffer from OSA that overcomes the shortcomings of conventional diagnostic devices and techniques. This object is achieved by providing an apparatus for reliably diagnosing the likelihood that the patient suffers from a breathing disorder, such as OSA, during a relatively short period of time and that is performed while the patient is awake, i.e., without the need for a sleep study. The diagnostic device of the present invention includes a first sensing system that determines a dimension of a portion of the patient's airway, such as the cross-sectional area, and an internal load determination system that determines an internal load imposed on the patient's airway. An internal load is the force acting on the inside walls of the patient's airways that tend to urge the airway to collapse, such as a negative pressure within the patient's airway relative to ambient atmospheric pressure. The internal load can be defined in terms of the negative pressure within the patient's airway relative to ambient pressure or in terms of the flow of gas within the airway, because there can exist a proportional, known, or determinable relationship between pressure and flow.

The diagnostic device of the present invention also includes a processing system that receives from the first sensing system and the internal load determination systems and determines a compliance curve that defines a relationship between the dimension information determined by the first sensing system and the different internal loads imposed on the patient's airway detected by the internal load determination system. The compliance curve is indicative of the compliance of the patient's airway because it represents how the dimensions of the airway change with changes in the internal load imposed on the airway. The processing system also determines at least one characteristic of the compliance curve, such as the slope and/or Y-intercept, indicative of a likelihood that the patient suffers from the breathing disorder.

It is a further object of the present invention to provide a diagnostic device that can be used to assess the likelihood that the patient suffers from a breathing disorder while the patient is seated and awake. In one embodiment, this object is achieved by using a device that applies an external load on the patient's airway while the patient is sitting, in conjunction with the diagnostic device discussed above. Providing an external load on the patient's airway enhances the ability of the diagnostic device discussed above to distinguish between OSA sufferers and non-OSA sufferers. Devices suitable to apply an external load on the patient's airway include: a neck collar with a selectively adjustable circumference, a neck collar with a selectively inflatable bladder that inflates to impose an external force on the patient's airway, and a neck cuirass that provides a chamber, which is sealed against the patient, so that providing a positive pressure greater than ambient atmospheric within the chamber likewise applies the positive pressure on the front exterior neck tissue of the patient.

In another embodiment of the present invention, assessing the likelihood that the patient suffers from a breathing disorder while the patient is seated and awake is achieved by providing a muscle stimulating device that stimulates the muscles associated with the patient's airway. The likelihood that the patient suffers from OSA can be determined by observing the patient's compliance curve in the absence of stimulation and in the presence of stimulation. There is less of a difference between the compliance curves in the presence and absence of muscle stimulation in OSA sufferers than in non-OSA sufferers. In other words, providing muscle stimulation has not significant effect on the compliance curve of an OSA sufferer. For a non-OSA sufferer, however, the muscle stimulation has a relatively large impact on the compliance curve. The more significant the difference between the two compliance curves, i.e., the compliance curve in the absence of muscle stimulation and the compliance curve in the presence of stimulation, the less likely it is that the patient suffers from OSA.

It is yet another object of the present invention to provide a diagnostic device that operates in conjunction with an mechanical device for providing an internal load on the patient's airway. In one embodiment, this is accomplished by providing a negative pressure generator and cuirass that delivers the negative pressure to the torso of the patient, thereby distending the patient's chest to create an inspiratory flow. In another embodiment of the present invention, an internal load is provided by applying an negative pressure to an airway of the patient. Using a mechanically generated internal load makes is possible to generate a uniform and easily controlled internal load in the patient's airway, while minimizing the patient's level of interaction needed to take the necessary measurements.

It is a still further object of the present invention to provide a method of diagnosing a breathing disorder that overcomes the shortcomings of conventional diagnostic methods. This object is achieved by providing a method for diagnosing a breathing disorder that includes the steps of causing a plurality of internal loads to be imposed on the patient's airway, determining an amount indicative of each internal load, determining a dimension, such the cross-sectional area, of the patient's airway at each internal load, determining a compliance curve indicative of the relationship between the dimension of the patient's airway and the plurality of the internal loads, and determining at least one characteristic associated with the compliance curve, such as the slope and/or Y-intercept, indicative of a likelihood that the patient suffers from a breathing disorder. In a further embodiment of the present invention, a mechanical device is used to generate an internal load on the airway of the patient, by, for example, providing an negative pressure to the airway of the patient or a chest distending force to the patient's chest area.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
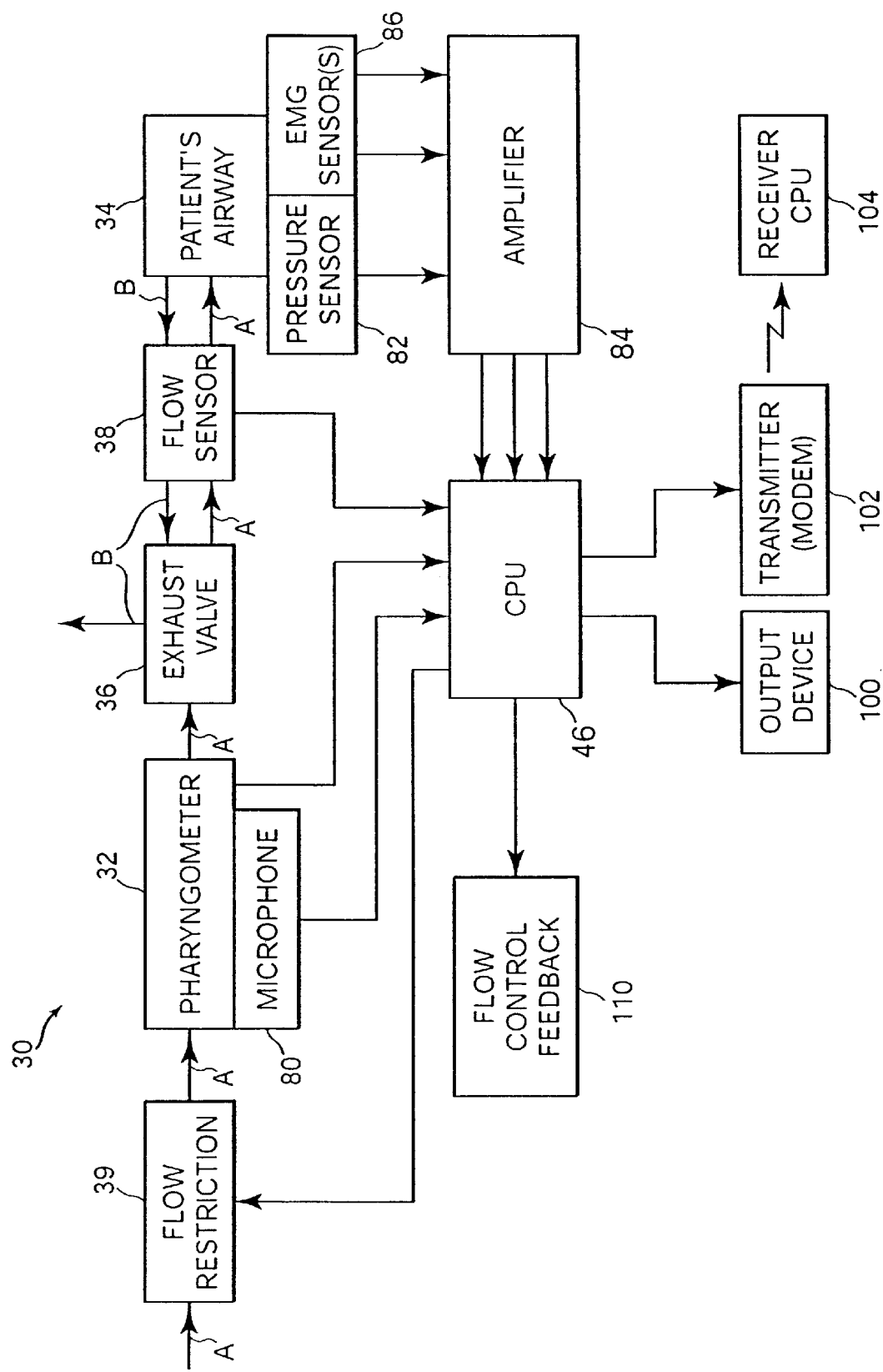
FIG. 1 is a schematic diagram of a diagnostic device according to the principles of the present invention.
Figure 2:
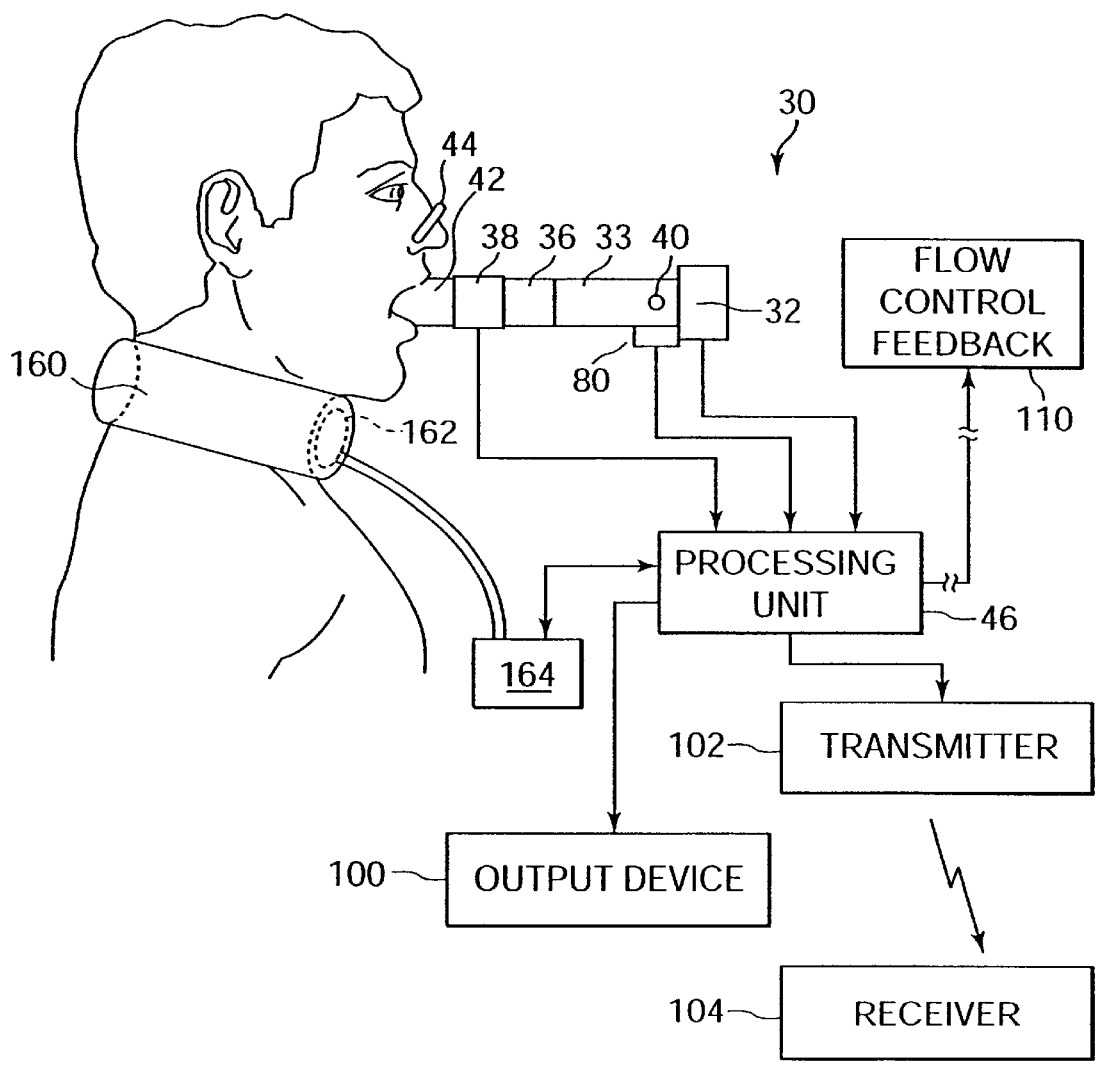
FIG. 2 is a schematic diagram illustrating the use of the diagnostic device generally shown in FIG. 1 on a patient.

FIGS. 1 and 2 schematically illustrate a diagnostic device 30 according to the principles of the present invention. There are slight differences between the devices illustrated in FIG. 1 and FIG. 2 to illustrate alternative embodiments and additional optional features of the present invention. The nature of these differences will become clear upon reviewing the following discussion.

The central features of diagnostic device 30 include: a first sensing system that determines a dimension of a portion of the patient's airway, an internal load determination system that determines an internal load imposed on the patient's airway, and a processor that, based on the information from the first sensing system and the internal load determination system, determines a likelihood that the patient suffers from a breathing disorder, such as OSA. In a preferred embodiment of the present invention, the dimension measured by the first sensing system is the cross-sectional area of the patient's airway. The present invention monitors the patient's airway compliance, which is the effect different internal loads and optional external loads have on the dimension of the patient's airway. As explained in greater detail below, the present inventors determined that compliance data can be used to determine the likelihood that the patient suffers from a breathing disorder, such as OSA.

It is known that the occurrence of OSA is the result of a collapse of a portion of the patient's airway during sleep. From this known phenomena, the present inventors initially surmised that the airway compliance of an OSA sufferer in an awake state would be greater than that of someone who does not suffer from OSA. That is, the present inventors suspected that a dimension, such as the cross-sectional area, of the airway of OSA sufferers while in an awake state, would be more likely to change with changes in an internal load placed on the airway than in non-OSA sufferers, due to the propensity of the airway in OSA sufferers to tend to collapse during sleep. In testing this hypothesis, however, the present inventors discovered that the opposite was true. The compliance of OSA sufferers in an awake state tends to be less than that of non-OSA sufferers. That is, the airway of OSA sufferers exhibits a smaller change in dimension, such as a change in cross-sectional area, with changes in an internal load placed thereon than non-OSA sufferers. This revelation is the basis for the diagnostic device and method of the present invention, which is essentially a device and method for imposing various internal loads on the airway and measuring the effects thereof to determine the patient's airway compliance. The less compliant the airway, the more like it is that the patient suffers from OSA.

For purposes of this invention, an "internal load" is any force acting on the airway walls that tends to cause the airway to collapse. For example, when the pressure within the airway is less than the ambient pressure outside the airway, an internal load in the form of a vacuum relative to the ambient atmosphere is created in the airway. The presence of this vacuum causes the inside surfaces of the patient's airway to collapse into the vacuum. There are several techniques in which an internal load can be applied to the airway of a patient.

One way to impose an internal load on the airway is to have the patient inspire (breathe in) through a flow restricting device. The inspiratory effort and flow restriction cause the pressure within the patient's airway to be less than the ambient pressure during inspiration, thereby creating an internal load in the form of a vacuum within the airway that tends to cause the airway to collapse. If the size of the flow restriction in the flow restricting device is constant, a greater inspiratory effort will create a higher negative pressure (relative to ambient atmosphere) in the patient's airway. Because pressure and flow are proportionally related, a greater inspiratory effort and, hence, more negative pressure within the patient's lungs and airway relative to ambient pressure, will result in a higher inspiratory flow rate, assuming the size of the restriction remains constant. Thus, increasing the patient's inspiratory effort while maintaining the size of the restriction constant will produce higher internal loads on the patient's airway, as evidenced by greater negative airway pressure relative to ambient pressure and a greater inspiratory flow rate. This technique uses a simple mechanism for providing the flow restriction. However, it requires that the patient control his or her inspiratory effort to maintain a relatively constant internal load during the airway measurement and increasing, decreasing or otherwise altering their respiratory effort to provide the different internal loads needed for the present invention.

It is possible to increase the internal load on the patient's airway by increasing the negative pressure within the airway relative to ambient pressure (and, hence, increasing the flow rate through the airway) without requiring the patient to increase his or her inspiratory effort. This can be accomplished, for example, by decreasing the size of the restriction through which the patient inspires while maintaining the patient inspiratory effort at the same level. If the inspiratory effort remains constant and the size of the restriction is decreased, a greater pressure will be developed within the patient and a greater inspiratory flow rate will result, without increasing the inspiratory effort required by the patient. This technique also uses a simple mechanism for providing the variable flow restriction. However, it also requires that the patient control his or her inspiratory effort to maintain a relatively constant internal load during the airway measurement and to use the same effort while different flow restrictions are imposed on the inspiratory flow. The present invention contemplates using either technique or a combination of both techniques for varying the internal load on the patient's airway.

In the embodiment illustrated in FIGS. 1 and 2, the first sensing system that determines a dimension, and, in particular, the cross-sectional area, of a portion of the patient's airway includes a two-microphone pharyngometer 32. Pharyngometer 32 communicates with a patient's airway 34 through an exhaust valve 36 and a flow sensor 38. The internal load determination system that determines the internal load imposed in the patient's airway, in this embodiment, includes flow sensor 38, which measures the flow rate of gas passing therethrough. As noted above, the flow rate of inspiratory gas is a measure of the internal load in the patient's airway due to the known or determinable relationship between pressure and flow.

Arrows A in FIG. 1 illustrate the flow of breathing gas during inspiration. Arrows B illustrate the path of gas during expiration. During inspiration, a breathing gas, such as air, passes through a flow restriction element 39 and enters a wave tube portion 33 of pharyngometer 32. In its simplest form, flow restriction element 39 is a hole 40 in wave tube 33 as shown in FIG. 2. It is to be understood that although only one hole 40 is illustrated in FIG. 2, more holes can be provided in wave tube 33 and/or hole 40 can have a variety of sizes depending on the desired degree of flow restriction.

In another embodiment of the present invention, the size of the opening to the wave tube provided by flow restriction element 39 is selectively variable to set the amount of flow restriction imposed on the inspired gas. For example, in the embodiment illustrated in FIG. 1, the degree of flow impedance imposed by flow restriction element 39 is controlled by a processor 46. It is to be understood, however, that the present invention also contemplates manually controlling the degree of the flow restriction. A variety of devices are suitable for use as flow restriction element 39. An example of a variable diameter flow restriction is a hole with a plate or adjustable iris that moves to cover, partially cover, or uncover the hole, with the plate or iris being moved by a motor under the control or processor 46 or under other independent controls.

Inspired gas travels from pharyngometer 32 through exhaust valve 36, thorough flow sensor 38 and into the patient's airway 34. As discussed below, pharyngometer 32 measures the cross-sectional areas along the patient's airway during the patient's inspiratory phase of the breathing cycle. However, during the expiratory phase of the breathing cycle, the expired gas should not travel back through the pharyngometer, because it will likely damage the sensitive microphones located in the wave tube. To avoid this result, the illustrated embodiment of the present invention causes the expired gas that travels through flow sensor 38 to be vented to ambient atmosphere through exhaust valve 38, so that substantially no gas enters pharyngometer 32 during expiration.

As shown in FIG. 2, one end of an assembly that includes pharyngometer 32, exhaust valve 36, and flow sensor 38 is placed into the mount of the patient. The patient closes his or her mouth and lips to provide a sealed airway. In the embodiment illustrated in FIG. 2, a mouthpiece 42 is provided at the end of the pharyngometer assembly to assist the patient in holding the end of the assembly in his or her mouth during the operation of the pharyngometer and to assist the system in providing a sealed airway. Mouthpiece 42 can have a variety of configurations. However, it is preferable that the diameter of the passageway through the mouthpiece substantially match the diameter of the wave tube portion of pharyngometer 32 to minimize the amount of reflections in the diagnostic device, thereby maximizing the performance of pharyngometer 32.

To facilitate providing a seal airway, the present invention contemplates clamping the patient's nostrils shut using a nasal clip 44, for example. However, other devices that accomplish the function of sealing off the patient's nares, such as nose plugs, are also suitable for use in the present invention. It should be understood that the patient's nostrils can be left open during the diagnostic procedure. Doing so, however, is likely to introduce noise and erroneous data into the diagnostic data. Therefore, although it is not necessary, it is preferable to seal the nasal passageways to maximize the performance of the pharyngometer.

Pharyngometer 32 uses an acoustic reflection technique to measure the cross-sectional area of at least a portion of the patient's upper airway during inspiration. More specifically, pharyngometer 32 continuously causes sound pulses to be propagated from a sound source along wave tube portion 33 of the pharyngometer through exhaust valve 36 and flow sensor 38 and into the airway of the patient. As the incident sound wave travels along the patient's airway, a reflection wave is generated due to the axial gradients in acoustic impedance within the airway. Both the incident and the reflected sound signals are recorded by microphones in the pharyngometer. These signals are output to a processing unit 46 that uses these signals to determine a cross-sectional area of the patient's airway along at least a portion of the length of the patient's airway. It is preferable that the diameters of exhaust valve 36, flow sensor 38, and mouthpiece 42 are substantially the same as that of wave tube portion 33 of pharyngometer 32 to minimize the calibration required by pharyngometer 32.

In a preferred embodiment of the present invention, pharyngometer 32 transmits acoustic pulses into the patient's airway and estimates the cross-sectional dimension of the airway every 200 msec. The cross-sectional areas are taken at increments of approximately 0.57 cm along at least a portion of the length of the airway. Processing unit 46 incrementally determines the cross sectional area of at least a portion of the airway in a direction away from the pharyngometer. In one embodiment of the present invention, the processing unit develops a plot of the results of the cross-sectional areas at each increment as a single continuous area curve.

Figure 3:
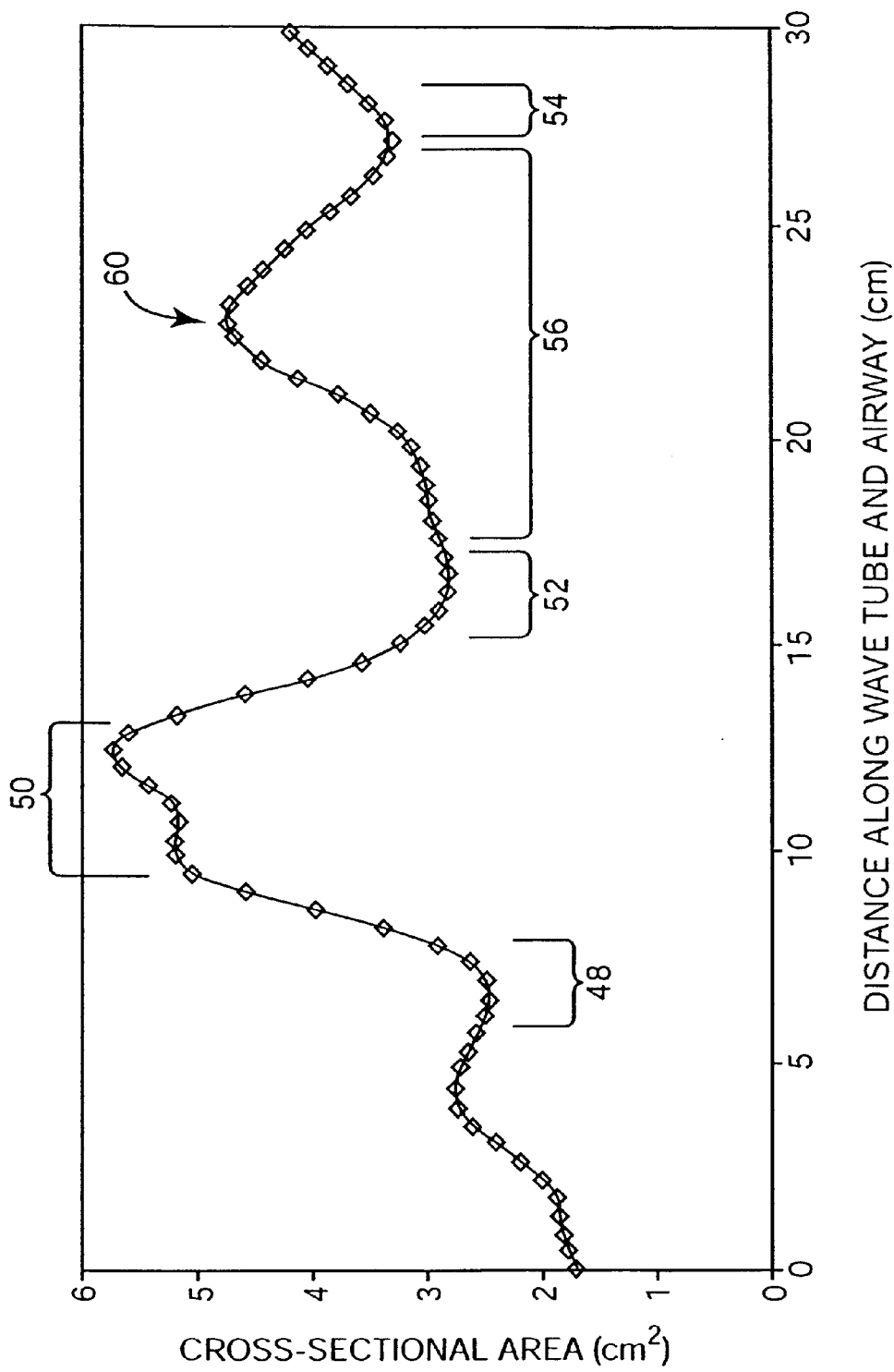
FIG. 3 is a chart illustrating the cross-sectional area of a portion of the patient's airway measured using the diagnostic device illustrated in FIGS. 1 and 2.

An example of such an area curve is illustrated in FIG. 3 where the horizontal axis represents the distance along the patient's airway and the vertical axis represents the cross-sectional area measured by the pharyngometer. Each diamond in FIG. 3 represents a cross-sectional area calculation point. Plotting the cross-sectional area of the portion of the airway of interest takes approximately 2.2 seconds, and thus, can be accomplished for most patients during a single inspiratory cycle. It is to be understood that the accuracy of the pharyngometer can be increased using conventional techniques, such as by increasing the sampling rate at which the pharyngometer estimates the cross-sectional areas so that the areas are taken at more closely spaced increments, thereby providing a more accurate determination of the cross-sectional area profile along the patient's airway.

For a more detailed discussion of a pharyngometer and its operation, please refer to the "Eccovision Acoutic Pharyngometry System Operator Manual," published by E. Benson Hood Laboratories, Inc., the contents of which are incorporated herein by reference. An example of a pharyngometer suitable for use in the present invention is the device manufactured by Hood Industries under the trade name, "Eccovision Acoustic Pharyngometry System." It is to be understood, however, that other pharyngometer devices, including one microphone pharyngometers, can be used in the present invention.

As shown in FIG. 3, the cross-sectional area of the airway of the patient, as represented by the y-axis, changes at known landmarks along the patient's airway. For example, the cross-sectional area decreases to a minimum at location 48 corresponding to the location of the patient's incisors. The cross-sectional area also increases to maximum at a location 50 corresponding to the patient's oral cavity, decreases to a minimum at location 52 corresponding to the oropharyngeal junction and at location 54 corresponding to the glottis. Oropharyngeal junction 52 and glottis 54 can usually be identified as the first and second minima in the cross-sectional areas of the airway following the relatively large cross-sectional area of the oral cavity. In general, the oropharyngeal junction is located approximately 10 cm beyond the incisors, and the oropharyngeal junction and glottis are typically located approximately 10 cm apart. These distances, however, vary slightly with the size of the patient's head.

The region of the airway between the oropharyngeal junction and the glottis is considered a collapsible portion 56 of the airway, because it is this portion of the airway that tends to collapse with changes in the internal load thereon. Thus, the present invention focuses on the compliance of this portion of the patient's airway. As shown in FIG. 3, the cross-sectional area of the airway in collapsible portion 56 generally increases from oropharyngeal junction 52 to a maximum cross-sectional area 60 and decreases thereafter.

Referring again to FIGS. 1 and 2, as noted above, the purpose of exhaust valve 36 is to vent expired gas, thereby preventing it from entering wave tube portion 33 of pharyngometer 32. If, however, the patient's nasal passages are not blocked by a nose clip or the like, at least during expiration, the patient may exhale through his or her nose rather than back through the pharyngometer assembly communicating with the patient's mouth, thereby eliminating the need for exhaust valve 36. This embodiment of the present invention, however, requires that the patient control his or her inspiration and expiration so that he or she breaths in through the mouth and out through the nose. This can be difficult for some patients to accomplish and/or difficult for some patients, such as those patient's with reduced or low mental capacities, to comprehend.

Although it is not believed to be presently available, if a pharyngometer can be developed that permits expired gas to pass through the wave tube without damaging the device, the patient's expired gasses can be vented through the flow restriction element, i.e., hole 40 in the end of the wave tube, thereby eliminating the need for exhaust valve 36. Until such time, however, a venting device, such as exhaust valve 36, or a technique, such as breathing out through the nose, is necessary to prevent expired gas from entering and possibly damaging the sensitive portions of the pharyngometer.

Figure 4A:
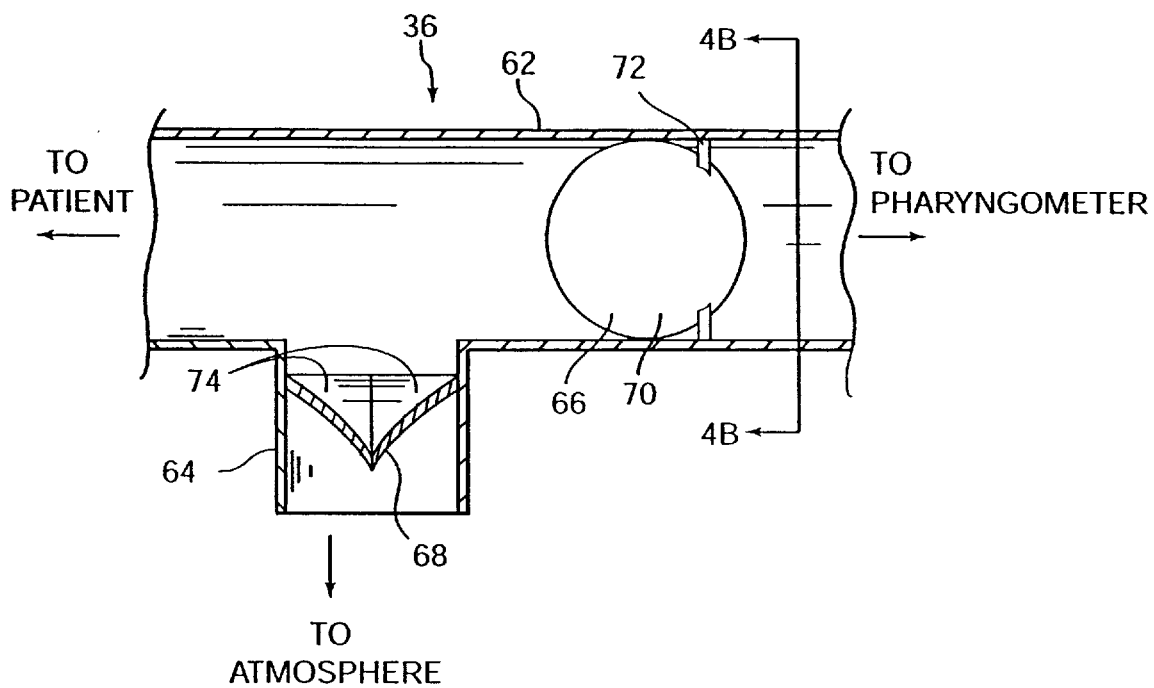
FIG. 4A is a diagram of an exhaust valve used in the diagnostic device illustrated in FIGS. 1 and 2.
Figure 4B:
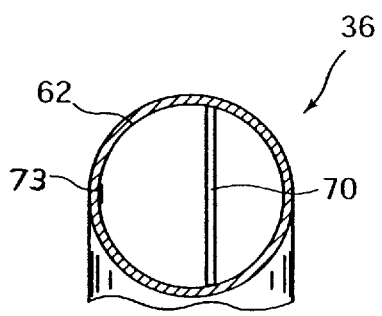
FIG. 4B is a cross-sectional view of a portion of the exhaust valve taken along line 4B—4B in FIG. 4A.

FIGS. 4A and 4B illustrate one embodiment for exhaust valve 36. It is to be understood, however, that exhaust valve 36 can have a variety of configurations and can include one or more valve elements located in a main gas passageway 62 and/or in an exhaust path 64 so long as the exhaust valve (1) passes gas from the pharyngometer to the patient during inspiration, (2) prevents gas from passing from the patient to the pharyngometer 32 during expiration, and (3) does not significantly alter or change the diameter or the direction of flow along the main gas passageway. Abrupt changes in the direction of flow between the pharyngometer and the patient are not easily handled by the pharyngometer data processing system.

Exhaust valve 36 in FIGS. 4A and 4B includes a first valve element 66 located in main passageway 62 and a second valve element 68 in exhaust path 64. First valve element 66 is a one-way check valve that allows gas to pass from the pharyngometer to the patient but does not allow gas to pass from the patient to the wave tube portion of the pharyngometer. In the illustrated embodiment, first valve element 66 includes a valve disk 70 eccentrically supported within main passageway 62 by a support member 72 offset from a centerline of the valve disk. The valve disk is rotateable about support member 72 between a first position (as shown in FIGS. 4A and 4B), wherein main gas passageway 62 is substantially open, and second position (not shown), wherein main gas passageway is substantially closed by disk 70. A stopper 73 maintains disk 70 in a position substantially blocking the main passageway against the force of the expired gas from the patient.

During inspiration, the inspired gas drawn in from the wave tube portion of the pharyngometer moves disk 70 from its closed position to an open position as shown in FIGS. 4A and 4B. In this open configuration, the blockage of the main passageway by the first valve element is minimized so that it does not impair the operating characteristics of the pharyngometer. More specifically, when the first valve element is open, only the edge profile of the disc, as shown in FIG. 4B, faces the pharyngometer. This minimizes acoustic reflections from the valve element and also minimizes the resistance to gas flow through the exhaust valve. During expiration, however, the offset rotational axis of disk 70 allows it to quickly move to a closed position substantially blocking the gas passageway. The cross-sectional areas of the patient's airway during the expiratory phase are not of interest. Therefore, it is unimportant that the main passageway is blocked by the first valve element during expiration.

Although first valve element 66 is described above and is illustrated in FIGS. 4A and 4B as being an eccentrically supported rotating valve disk, the present invention is not limited to this configuration. Any valve element that provides the functions of a one-way check valve while presenting a minimal reflective surface in an open state (during inspiration) without substantially altering the diameter or flow direction is suitable for this invention.

Second valve element 68 is a one-way check valve that permits gas to flow from the patient to the ambient atmosphere during expiration and does not permit gas to flow from atmosphere to the patient during inspiration. In the illustrated embodiment, second valve element 68 is a flap valve having a plurality of flaps 74 with first ends fixed to the wall of exhaust path 64 and second ends converging at the center of the exhaust path. Flaps 74 are biased to be in a closed position when there is no flow, i.e., no pressure differential between atmosphere and the main passageway. During inspiration, flaps 74 remain closed, as illustrated in FIG. 4A, to prevent gas from being drawn from the atmosphere into the main passageway by the patient's inspiration. The closure of flaps 74 also serves to maintain a sealed airway to optimize the operation of the pharyngometer. During expiration, flaps 74 are separated by the force of the expired gas, allowing the expired gas to vent to atmosphere.

While one embodiment of second valve element 68 is described above and illustrated in FIG. 4A, it is to be understood that other configurations for second valve element 68 are contemplated by the present invention. Any one-way check valve that performs the above described functions of second valve element 68 is suitable for the present invention. For example, second valve element 68 can be any one of the following: a ball valve, a butterfly valve, a duckbill valve, or a flap valve similar to that used as first valve element 66. This list is by no means exclusive. Furthermore, it is to be understood that other configurations for the overall structure of exhaust valve 36 are contemplated by the present invention. The invention is not intended to be limited to the two-valve element configuration discussed above and illustrated in FIGS. 4A and 4B. On the contrary, any valve arrangement can be used for exhaust valve 36 so long as the functions discussed above are obtained.

Referring again to FIGS. 1 and 2, as noted above, flow meter 38 measures the rate of flow of gas passing therethrough and, hence, the rate of flow of gas passing through the patient's airway. For a given size restriction, the different flow rates correspond to different negative pressures within the patient's airway relative to the ambient pressure, and, hence, different internal loads on the patient's airway. Thus, the flow rate measured by flow meter 38 is an indication of the internal load imposed on the patient's airway.

Flow meter 38 can be any device suitable to measure patient flow. As shown in FIGS. 1 and 2, flow meter 38 is provided between exhaust valve 36 and the end of the assembly that communicates with the patient's airway. This configuration is advantageous because it enables flow meter 38 to detect both inspiration and expiration. By detecting inspiration, processor 46 can coordinate the data received from the flow meter and the pharyngometer so that the flow rate (internal load) and the airway cross-sectional areas associated with that flow rate can be obtained.

It should be understood, however, that other arrangements for flow meter 38 and exhaust valve 36 are contemplated by the present invention. For example, flow meter 38 and exhaust valve 36 can be reversed from their positions illustrated in FIGS. 1 and 2 so that exhaust valve 36 is adjacent the distal end of the portion of diagnostic device 30 that contacts the patient. In this alternative configuration, exhaust valve 36 vents the expired gas to atmosphere and little, if any, expired gas passes through the flow meter. Thus, flow meter 38 does not provide a reasonable estimation of the rate of expired gas from the patient. This alternative configuration is advantageous, however, because it reduces the amount of dead space between the patient's lungs and the exhaust vent otherwise included in flow meter 38, thereby reducing the amount of $CO_2$ rebreathing by the patient.

The present invention also contemplates providing the flow meter so that it measures the flow through flow restriction 39, rather than being placed in-line with wave tube portion 33 of pharyngometer 32. For example, the present invention contemplates providing flow meter 38 adjacent to hole 40 so the flow of gas entering hole 40 is measured by the flow meter.

In one embodiment of the present invention, flow meter 38 is a pneumotach flow meter, which is a pressure based device that measures a pressure differential across a flow element in the main gas passageway through the pneumotach. This pressure differential signal is provided to processor 46 so that the flow through the pneumotach can be determined using well known techniques, which are based on the known relationship between pressure and flow. An example of a suitable pressure-based pneumotach flow meter is the pneumotachometer manufactured by Fleish, Inc. or Model No. 4700 manufactured by Hans Rudolph of Kansas City, USA.

In another embodiment of the present invention, flow meter 38 is a bypass type device in which a portion of the flow of gas in the main passageway is bypassed through a relatively small bypass circuit. The bypass circuit connects to the main passageway across a flow element so that the bypass circuit is generally in parallel with the main gas passageway. A relatively small portion of the gas travels through the bypass passage due to the pressure drop in the main passage across the flow element. An airflow sensor, such as a Honeywell AMV2000, measures the rate of flow through the bypass circuit. The known flow rate through the bypass circuit can then be used to determine the overall flow rate through the main passageway.

As noted above, both ends of the bypass circuit can be connected across a flow element so that the airflow sensor in the bypass circuit measures the flow rate of gas through bypass circuit caused by the flow element. In an alternative embodiment, only one end of the bypass circuit is connected to the breathing circuit, the other end being open to atmosphere. The airflow sensor in the bypass circuit of this embodiment measures the flow rate through the bypass circuit with an airflow sensor and determines the flow rate of gas through the main passageway using conventional techniques.

Although two types of airflow sensors, one pressure based and one bypass flow based, are described above, the present invention is not intended to be limited to these particular types of flow sensors. Any device that is capable of measuring the flow of gas at the patient is suitable for use in the present invention.

In the illustrated embodiment, diagnostic device 30 includes an external microphone 80 that records sounds generated by the pharyngometer and provides signals indicative thereof to processing unit 46. In this embodiment of the present invention, the signals from microphone 80 are used to correlate the cross-sectional area data produced by pharayngometer 32 with the flow data produced by the flow sensor 38, as discussed in greater detail below. If the pharyngometer and flow sensor data are correlated with one another, for example by controlling the operation of the pharyngometer and flow sensor using a processing unit, microphone 80 can be eliminated.

Diagnostic device 30 illustrated in FIG. 1 also includes a pressure sensor 82 that measures the pressure within the patient's airway. This is typically accomplished by placing one end of a hollow tube within the sealed airway, with the other end connected to a pressure transducer outside the patient. For example, a pressure port can be provided in the mouthpiece, exhaust valve 36, flow sensor 38 and/or wave tube portion 33 to which the hollow tube is connected. The signal output from pressure sensor 82 is provided to an amplifier 84, and the amplified signal is provided to processor 46. Note that pressure sensor 82 is omitted from illustration in FIG. 2.

Pressure sensor 82, like flow sensor 38, provides an indication of the internal load imposed on the patient's airway. Because pressure and flow are related, either the pressure sensing system or the flow sensing system described above is suitable for purposes of measuring the load imposed on the patient's airway. However, the present invention contemplates using both types of sensors for redundancy and data checking purposes, for example.

Although not necessary for purposes of the present invention, the diagnostic device of FIG. 1 also includes an electromyogram ("EMG") sensor 86 that detects the activity of muscles associated with the airway, such as the geniohyoid, sternohyoid, and sternothyroid muscles. The signals output from EMG sensor 86 are provided to an amplifier 84 and the amplified signals are output to processor 46. This information may be helpful to some medical personnel because it provides a measure the activity of the muscles associated with the upper airway. However, as noted above, this information is not necessary in the present invention in determining the likelihood that the patient suffers from a breathing disorder, such as OSA. Note that EMG sensor 86 is omitted from illustration in FIG. 2.

Figure 5:
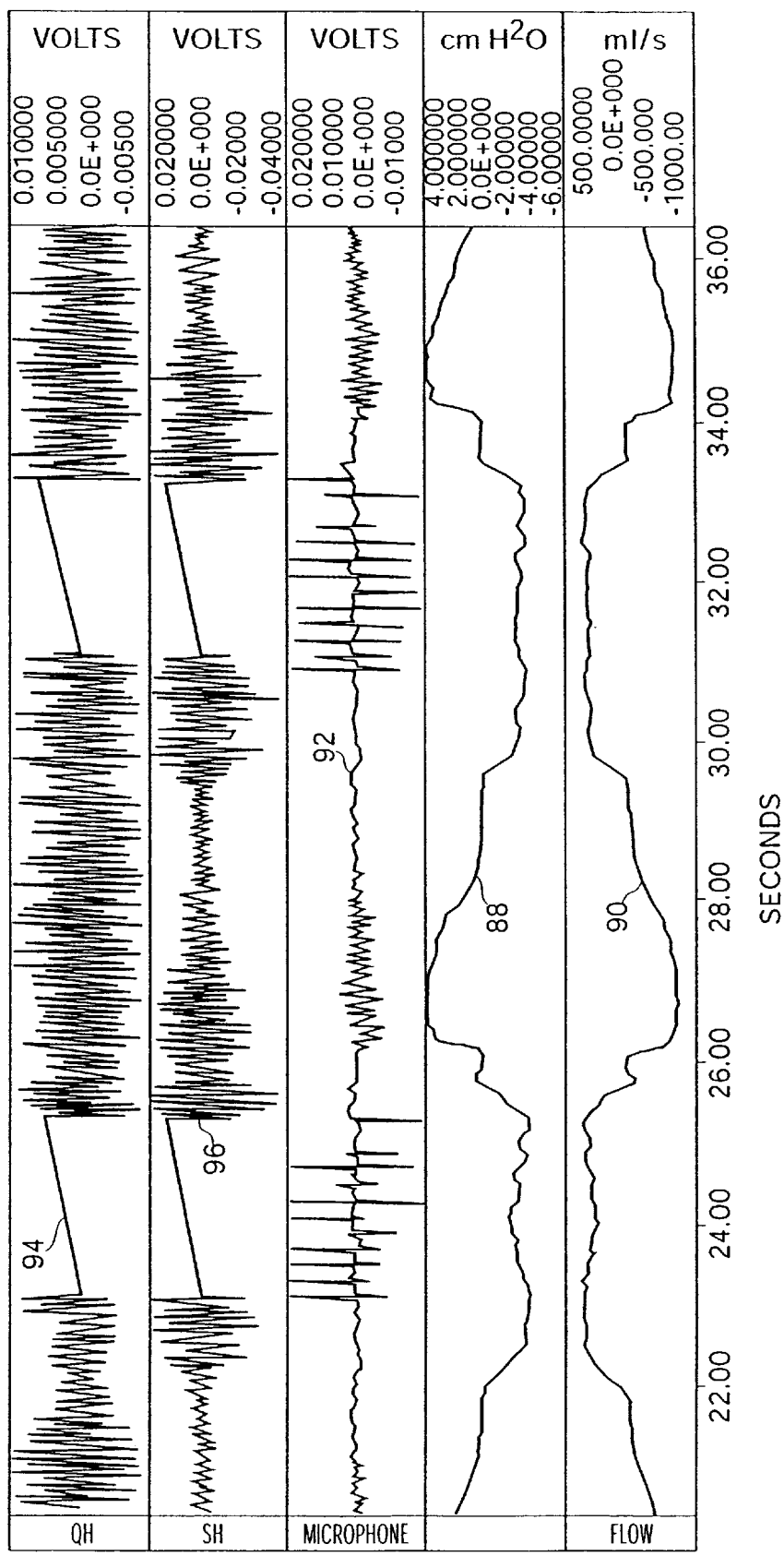
FIG. 5 is a chart illustrating the data collected from various sensors using the device illustrated in FIG. 1.

In one embodiment of the present invention, processor 46 includes a multi-channel recorder capable of storing data in time-based synchronization from a plurality of sources. FIG. 5 is an example of the different types of information provided from various sensing devices that are stored in time-based synchronization in such a multi-channel recorder. In FIG. 5, waveform 88 illustrates the signal output from flow meter 38, waveform 90 illustrates the signal output from pressure sensor 82, waveform 92 illustrates the output from microphone 80, and waveforms 94 and 96 illustrate the output from EMG sensors 86. There are two waveforms 94 and 96 in FIG. 5 because this experiment utilized two EMG sensors corresponding to two different muscles or muscle groups associated with the upper airway.

Storing the information from a plurality of sources in time based synchronization enables the data from different sources collected individually to be correlated with one another. In the present embodiment, for example, it is necessary to correlate the data from the pharyngometer with that of the flow meter and/or pressure sensor. This is important, for example, because one embodiment of the present invention contemplates that the functions of pharyngometer 32 and flow sensor 38 (or pressure sensor 82) take place independently. In which case, the respective results of the pharyngometer and flow sensor (or pressure sensor) must be correlated with one another. The signals output from microphone 80 provide an indication of when the pharyngometer is taking its readings so that the flow rate data (or pressure data) for that period can be determined.

As shown in FIGS. 1 and 2, a preferred embodiment of diagnostic device 30 includes an output device 100 to provide the information garnered from the various sensing devices, as well as information determined by processor 46, in human perceivable format or to other external devices. Examples of devices that can serve as output device 100 include a printer, display, and audio device. Of course, more than one type of output device can be provided and any conventional type of device is contemplated for use with the present invention.

FIGS. 1 and 2 also illustrate a transmitter 102 coupled to processor 46. Transmitter 102 communicates the data from the various sensing devices and/or the information determined by processor 46 to a remote receiver 104. The transmission can be wireless, as shown in FIGS. 1 and 2, via a hardwire, or a combination thereof. For example, transmitter 102 can be a modem that communicates using conventional telephony technology. It is to understood, however, that the present invention is not intended to be limited to the output devices discussed above. Quite the contrary, all conventional output devices and any device that accomplishes the function of outputting information is a suitable output device for purposes of the present invention.

The operation of diagnostic device 30 requires measuring at least one cross-sectional area for each of a plurality of internal loads imposed on the patient's airway. There are two ways discussed above to alter the internal load on the patient's airway: 1) have the patient inspire through a single-size restriction at different levels of inspiratory effort, or 2) have the patient inspire through different sized restrictions at the same level of inspiratory effort. Using either technique, the patient controls the rate at which he or she breathes in to match the desired flow rate necessary to achieve the desired internal load. The first method is advantageous because it simplifies the structure of the diagnostic device. However, as noted above, the first technique is disadvantageous in that it requires that the patient inspire at different rates, which can be difficult for a patient to learn and accomplish and time consuming to teach to the patient. The second technique requires a relatively more complicated diagnostic device with the capability to vary the size of hole 40, for example. However, it is advantageous in the that it is generally easier for the patient to maintain his or her inspiratory effort at a constant level during each cross-sectional area measurement cycle than vary the inspiratory effort.

To assist the patient in controlling his or her inspiratory rate, regardless of the technique used to alter the internal load on the airway, a further embodiment of the present invention provides a flow control feedback device 110. This device provides the patient with an indication of the target inspiratory flow rate (or target inspiratory pressure) and the current inspiratory flow rate (or current inspiratory pressure). The patient controls their level of inspiratory effort so as to cause the current inspiratory flow rate (or current inspiratory oral pressure) to match the target inspiratory flow rate (or target inspiratory oral pressure).

In one embodiment of the present invention, the target flow rate (target pressure) is varied and the size of the restriction is kept constant. The patient is instructed to inspire at a flow rate (pressure) matching the target flow rate (pressure) so that the pharyngometer can obtain a cross-sectional profile of at least a portion of the patient's airway at that flow rate (pressures), which ideally matches the target rate. In another embodiment, the target flow rate (target pressure) is kept constant and the size of the restriction is varied. The patient is instructed to inspire at a flow rate (pressure) matching the target flow rate (pressure) so that the pharyngometer obtains a cross-sectional profile of at least a portion of the patient's airway at that flow rate (pressure), which ideally matches the target flow rate (pressure). Either procedure assures that different internal loads are imposed on the patient's airway so that the cross-sectional area of at least a portion of the patient's airway can be measured at each of a plurality of different internal loads.

One example of a flow control feedback device 110 includes two columns of light emitting diodes ("LEDs"). The LEDs in one column light in an ascending manner commensurate with the flow rate of gas through the flow meter, thereby indicating the current inspiratory flow rate. The LEDs in the other column remain lit to a level commensurate with the target rate. In operation, the patient controls his or her inspiratory effort to maintain the lit LEDs in the two columns at the same level. Raising or lowering the target level provides the patient with an indication of different flow rates that are needed to impose different internal loads on the patient assuming the size of the flow restrictions remains constant. Even if the size of the flow restriction is altered to provide different internal loads on the airway, it is still necessary that the patient inspire at a constant rate for each set of readings. The flow control feed back device facilitates this function.

It is to be understood that the present invention is not intended to be limited to the specific type of flow control feedback device discussed above. On the contrary, any device that provides the patient with an indication of the current internal load (as measured by flow or pressure) and an indication of the target internal load, so that the patient can control his or her effort to match the two is suitable for the present invention. The internal load indicators can be visual, such as a match-needle type device, or audio, such as a variable frequency sound indicative of the current internal load and a second fixed frequency sound indicative of the target internal load.

The present invention also contemplates operating the diagnostic device such that the patient does not have to control his or her breathing so that he or she breathes at a constant rate, and, hence, produces a constant internal load on the airway, while the pharayngometer measures the area of their airway. Instead, the patient breathes normally, and the diagnostic device takes the cross sectional area at various points in the breathing cycle and, if necessary, accumulate flow and cross-sectional area date from multiple breathing cycles in order to measure the internal load on the patient and the corresponding cross-sectional area. For example, the present invention contemplates providing a first flow restriction of a first size and having the patient breathing normally through that flow restriction. As the patient breathes normally, the inspiratory flow rate will vary. The present invention contemplates operating pharyngometer 32 and/or processor 46 so that one or more cross-sectional areas are measured when the flow rate is at the desired rate. This can be accomplished, for example, by taking the cross-sectional area at different portions of the breathing cycle. For example, each time the patient breathes in, at some point (and perhaps more than one point) during the inspiratory phase, their actual inspiratory flow rate corresponds to the desired flow rate at which the cross-sectional area of the airway is to be measured. If the patient's inspiratory flow rate is at the desired flow rate for enough time during the inspiratory phase, the pharyngometer can measure the cross-sectional areas during these times and produce a diagram as shown in FIG. 3 for the internal load set by the size of the flow restriction. Changing the size of the flow restriction can then be used to change the internal load to accumulate a plurality of waveforms, such as those shown in FIG. 5.

Using current pharangometry techniques, however, it is unlikely that the cross-sectional area along the desired length of airway can be accurately measured in the relatively short time that the patient's inspiratory flow rate matches the desired flow rate. To solve this problem, the present invention contemplates accumulating the cross-sectional areas taken during the portion of the patient's inspiratory cycle while he or she is inspiring at the target inspiratory flow rate from a number of breathing cycles. This accumulation of cross-sectional areas can then be combined to determine the cross-sectional area along at least a portion of the patient's airway for a common inspiratory flow rate even while the patient breathes normally, i.e., at a non-constant rate over the course of the inspiratory phase. Such a waveform corresponds to that shown in FIG. 3. Of course, this need to accumulate the cross-sectional area from multiple inspirations can be eliminated or reduced if the sampling speed of the pharyngometer is improved so that more cross-sectional area measurements can be taken in a shorter period time. Thereafter, the size of the flow restriction can be changed and the process repeated to accumulate a number of cross-sectional area curves for each internal load (flow restriction), as shown, for example, in FIG. 5.

Figure 6:
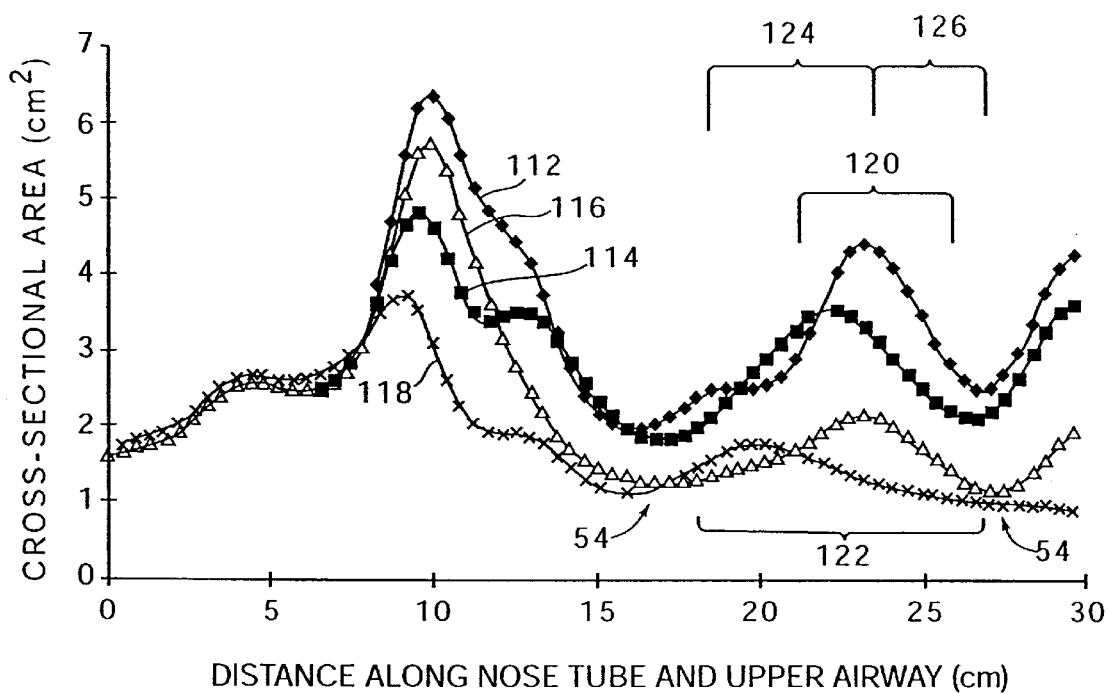
FIG. 6 is a chart illustrating the cross-sectional areas of an upper airway of a patient measured using the diagnostic device illustrated in FIG. 1 while the patient inspires at various flow rates.

FIG. 6 is a chart illustrating the cross-sectional areas of an upper airway of a patient measured using the diagnostic device illustrated in FIG. 1 while the patient inspires at various flow rates. Waveform 112 corresponds to the cross-sectional pharyngeal areas along the patient's airway while the patient is at rest (inspiring at a substantially 0 ml/sec). Waveform 114 corresponds to the cross-sectional pharyngeal areas while the patient is inspiring at approximately 100 ml/sec. Waveform 116 corresponds to the cross-sectional pharyngeal areas while the patient is inspiring at approximately 300 ml/sec. Finally, waveform 118 corresponds to the cross-sectional pharyngeal areas while the patient is inspiring at approximately 500 ml/sec. It is to be understood that the horizontal axis could identify the pressure in the airway rather than flow, due to the relationship between pressure and flow.

From FIG. 6, it can appreciated that, in general, the cross-sectional area over a portion 120 of the patient's airway tends to decrease as the patient's inspiratory flow rate increases. It can be further appreciate that portion 120 is within collapsible portion 122, which extends generally between oropharyngeal junction 52 and glottis 54. In this embodiment, the size of the restriction in the wave tube portion of the pharyngometer was kept constant so that greater inspiratory flows corresponds to greater internal loads on the patient's airway. The increased internal load on the patient's airway induced a general decrease in the average cross-sectional area over the collapsible portion of the patient's airway. The greater the change in average cross-sectional area with respect to the changes in the internal load, the more compliant the patient's airway and vice versa.

In a preferred embodiment of the present invention, the processor averages the cross-sectional areas of the patient over the collapsible portion of the airway. The resultant average valve of the cross-sectional areas over the collapsible portion is referred to as the mean pharyngeal area ("MPA"). A decrease in the MPA indicates a collapse of the portion of the patient's airway over which the cross-sectional areas are being averaged. It is also possible to average the cross-sectional area over any portion of the patient's airway, such as a sub-portion of the collapsible portion.

Determining the portion of the airway over which to average the cross-sectional areas can be done using a variety of techniques. In a relatively simple embodiment of the present invention, the operator selects, based on the cross-sectional areas output from the pharyngometer, the portion of the patient's airway over which the cross-sectional area are to be averaged. This is done, for example, by identifying the collapsible portion (or a portion of the collapsible portion) of the patient's airway from the pharyngometer data. See the above discussion with respect to FIG. 3. It is preferable to use the cross-sectional area information corresponding to a relatively low internal load (a low flow rate) because this information is believed to provide the clearest indication of the collapsible portion of the airway. For example, line 112 in FIG. 3 has more pronounced features than line 118, which corresponds to a higher flow rate.

In another embodiment of the present invention, processor 46 identifies the collapsible portion (or a portion of the collapsible portion) from the cross-sectional area profile data without requiring the operator to select the relevant portion of the cross-sectional area profile. This can be accomplished, for example, by programming the computer to identify landmarks in the pharyngometer output pattern, and from these landmarks, determine the position of the collapsible portion (or a portion of the collapsible portion) of the patient's airway.

Yet another embodiment of the present invention contemplates that the portion of the cross-sectional area profile over which the cross-sectional area are to be averaged can be determined based on distance. For example, it is known that, in general, the oropharyngeal junction is located approximately 10 cm beyond the incisors, and the oropharyngeal junction and glottis are typically located approximately 10 cm apart. The processor can use these known distances and average the cross-sectional area information in a range of 10–20 cm from the patient's incisors, for example. However, because these distances typically vary slightly with the size of the patient's head, the present invention further contemplates refining the distance-based determination of the location of the collapsible portion (or a portion of the collapsible portion) of the patient's airway over which the cross-sectional area are to be averaged by taking into consideration the patient's head size. This is accomplished, for example, by measuring the patient's head and inputting this information to the diagnostic device. Processor 46 takes this information into consideration, using a look-up table, for example, in determining the portion of the airway over which the cross-sectional area are to be averaged.

Although the present invention has been described above as taking an average of the cross-sectional areas over the collapsible portion or over a portion of the collapsible portion of the patient's airway, the present invention also contemplates taking an average of the cross-sectional areas over more than one portion of the patient's airway. For example, in one embodiment of the present invention, the diagnostic device divides the collapsible portion of the airway into an upper region, such as region 124 in FIG. 6, and a lower region, such as region 126 in FIG. 6, the upper region being closer to the patient's mouth than the lower region. This embodiment of the present invention averages the cross-sectional areas over upper region 124 and lower region 126 individually, so that changes in the mean cross-sectional area for each region associated with changes in the internal load can be studied separately. This information may provide a more accurate indication of the likely location of obstructions so that treatment techniques can be selected that focus on the area of the patient's airway that is obstructing. It is to be understood that the patient's airway can be segmented into any number of regions, with a mean cross-sectional area being taken for each region, to study the mechanics of the airway, and, in particular, the effects of different internal loads on each region individually.

Figure 7:
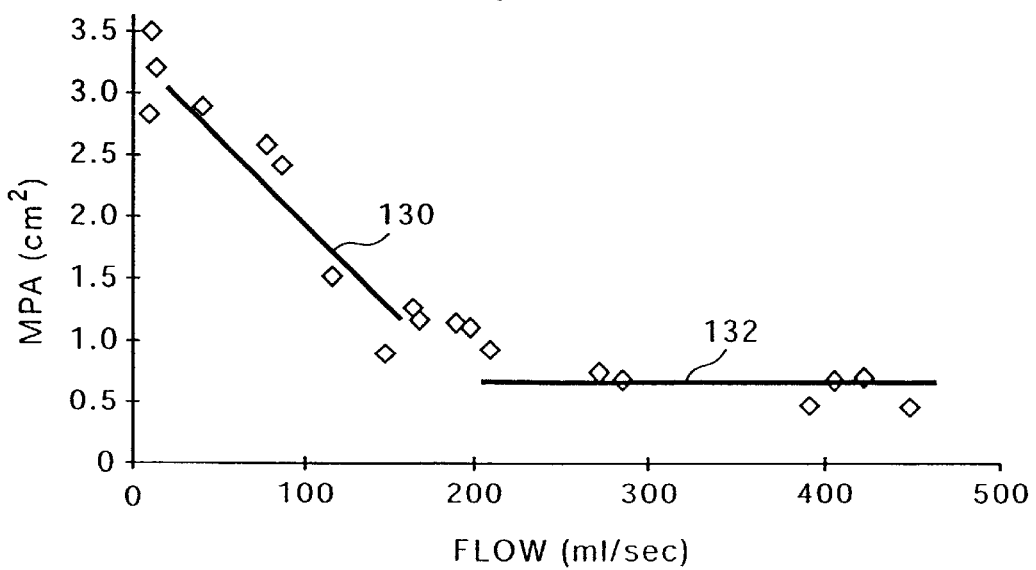
FIG. 7 is a chart illustrating the relationship between the measured mean pharyngeal area of a patient at a variety of flow rates (internal loads)

In addition to studying the correct portion of the airway to monitor for collapse, or lack or collapse, it is also preferable to limit the internal loads imposed on the airway to a relatively low level for reasons that are explained below with reference to FIG. 7. FIG. 7 is a chart illustrating the relationship between the measured mean pharyngeal area of the collapsible portion of a patient's airway at a variety of flow rates, e.g., internal loads. FIG. 7 demonstrates that, in general, the greatest changes in cross-sectional area occur at relatively low flow rates, i.e., while relatively low internal loads are being imposed on the airway. Line 130 is a linear regression line approximating the relationship between MPA and flow at relatively low flow rates, and line 132 is a linear regression line that approximates the relationship between MPA and flow at relative high flow rates. Lines 130 and 132 are indicative of the compliance of the airway over the specified range of internal loads (flow rates in this embodiment).

It can be appreciated from FIG. 7, that the slope of line 130 is greater than that of line 132, indicating that the MPA changes more rapidly during changes in the internal load that take place at relatively low flow rates (i.e., low internal loads) than changes in the internal load that take place at relatively high flow rates (i.e., relatively high internal loads). Stated another way, the compliance is generally greater over a range of relatively low internal loads (flow rates) than over a range of high internal loads. For this reason, the present invention focuses on the changes in cross-sectional area associated with changes in relatively low internal loads, such as those occurring at flow rates of 300 ml/sec or less.

Figure 8:
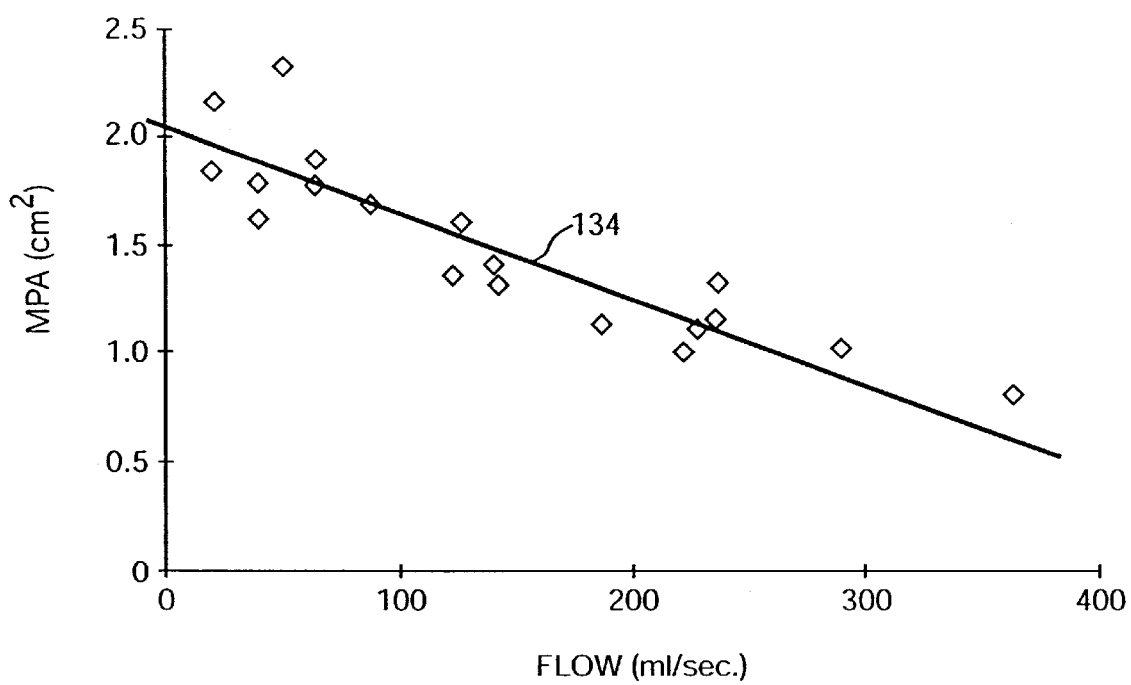
FIG. 8 is a chart illustrating the relationship between the measured mean pharyngeal area of a patient that does not suffer from a breathing disorder measured at a variety of flow rates.
Figure 9:
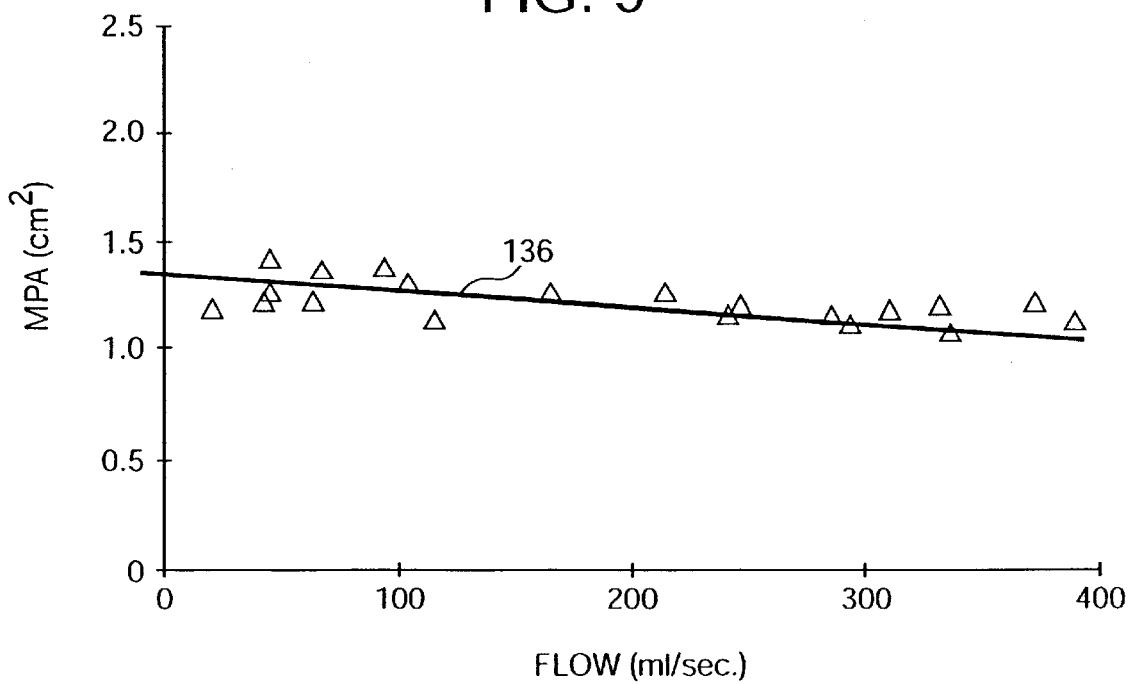
FIG. 9 is a chart illustrating the relationship between the measured mean pharyngeal area of a patient that suffers from a breathing disorder measured at a variety of flow rates.

FIG. 8 is a chart of the MPA measured at a variety of flow rates, i.e., internal loads, for a patient that does not suffer from OSA. FIG. 9 is chart of the measured MPA at a variety of flow rates for a patient that suffers from OSA. Comparing FIGS. 8 and 9, it can be appreciated that patients not suffering from OSA (FIG. 8) tend to experience greater changes in MPA, especially at low flow rates (low internal loads) between 0–300 ml/sec (negative pressures of 0 to −2.4 cm $H_2O$), than patients suffering from OSA (FIG. 9). In other words, the airway in a patient suffering from OSA is less compliant than the airway in a patient who does not have OSA. This phenomena is perhaps best illustrated by comparing line 134 in FIG. 8 and line 136 in FIG. 9, which are compliance curves determined by a linear regression analysis of the data plotted in these figures. Lines 134 and 136 are referred to as compliance curves because they are indicative of the relationship of MPA versus flow rate (internal load), which corresponds to the compliance of the patient's airway. Line 134 is typical of patients that do not suffer from OSA, and line 136 is typical of patients that suffers from OSA.

Compliance curve 134 in FIG. 8 for a non-OSA sufferer has a slope, albeit a negative slope, that is greater than the slope of compliance curve 136 for a patient that suffers from OSA. Furthermore, the Y-intercept of compliance curve 134, which corresponds to the MPA at a 0 flow rate, or when no internal load is imposed on the patient's airway, is greater than the Y-intercept of line 136. Either or both of these characteristics of the compliance curve for each type of patient are used by the present invention to differentiate between a patient who suffers from OSA and a patient who does not suffer from OSA. For example, the smaller the slope of compliance curve 134 or 136 corresponding to a relationship of the cross-sectional area versus the plurality of internal loads, the more likely the patient suffers from OSA. Also, the lower the Y-intercept of that line, the more likely the patient suffers from OSA.

Figure 10:
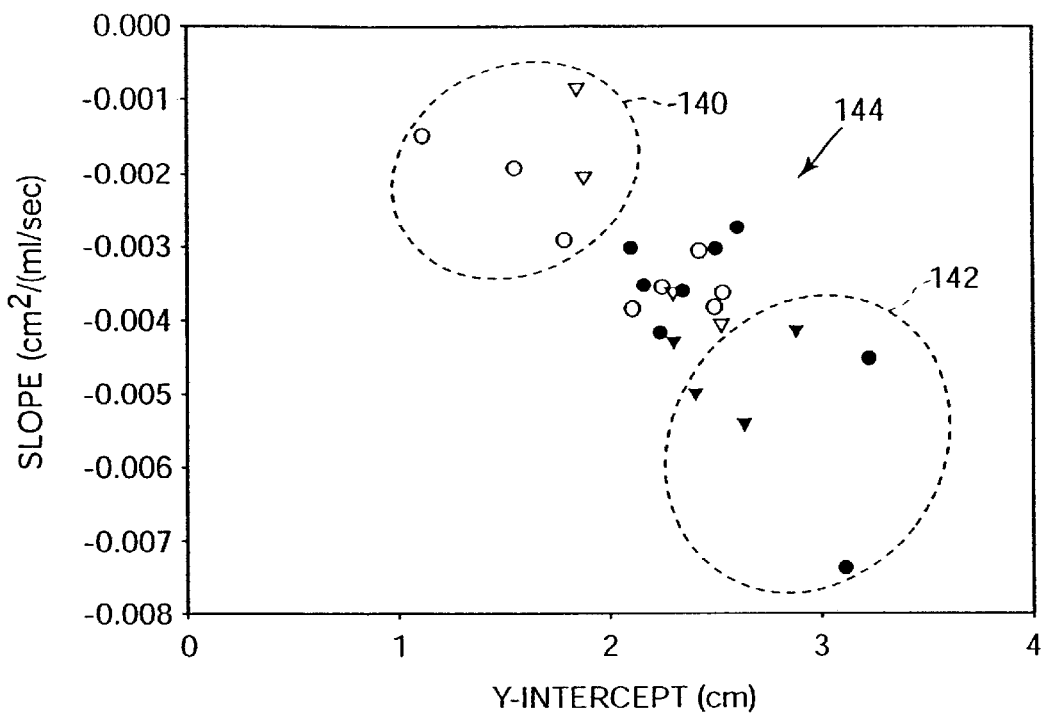
FIG. 10 is a chart illustrating the relationship between the Y-intercept and the slope characteristics determined from a compliance curve defined using a statistical analysis of the mean pharyngeal area versus flow rate relationship for a variety of patients, where the mean pharyngeal area and flow rate information are taken while the patients are sitting.

FIG. 10 is chart illustrating the relationship between the Y-intercept and the slope characteristics determined from the statistical analysis of the mean pharyngeal area versus flow rate relationship for a variety of patients, i.e., from the compliance curves of a variety of patients. The white circles and white inverted triangles correspond to patients who are known OSA sufferers, and the solid circles and solid inverted triangles correspond to patients who have been determined to not suffer from OSA. The data in FIG. 10 was taken while the patients were seated. FIG. 10 demonstrates that if the slope of the compliance curve for a patient is relatively low and the Y-intercept of the compliance curve is also relatively low, the patient is likely to suffer from OSA. Conversely, if the slope of the compliance curve is relatively high and the Y-intercept is relatively high, the patient is less likely to suffer from OSA.

From FIG. 10 and the above discussion thereof, it can be appreciated that the prescreening technique of this embodiment is perhaps best suited to differentiate those patient's at each extreme; patients with very compliant airways under a plurality of internal loads (high slope and high Y-intercept) indicated as group 140 in FIG. 10 and patients with non-compliant airways under the same internal loads (low slope and low Y-intercept) indicated as group 142. The former are very likely to suffer from OSA and the latter are not. There are, however, are relatively large number of patients, generally indicated at 144, that fall between these two extremes.

To differentiate OSA sufferers from normal patients more clearly, the present invention provides a further technique of introducing an external load on the patient's airway. For present purposes, an external load in any force acting on the airway that tends to cause the airway to collapse other than a negative pressure within the airway, which, as defined above, is an internal load. The present inventors discovered that providing an external load on the airway tends to decrease the airway compliance under a plurality of internal loads for patients suffering from OSA and tends to enhance airway compliance under a plurality of internal loads for patients that do not have OSA.

Figure 11:
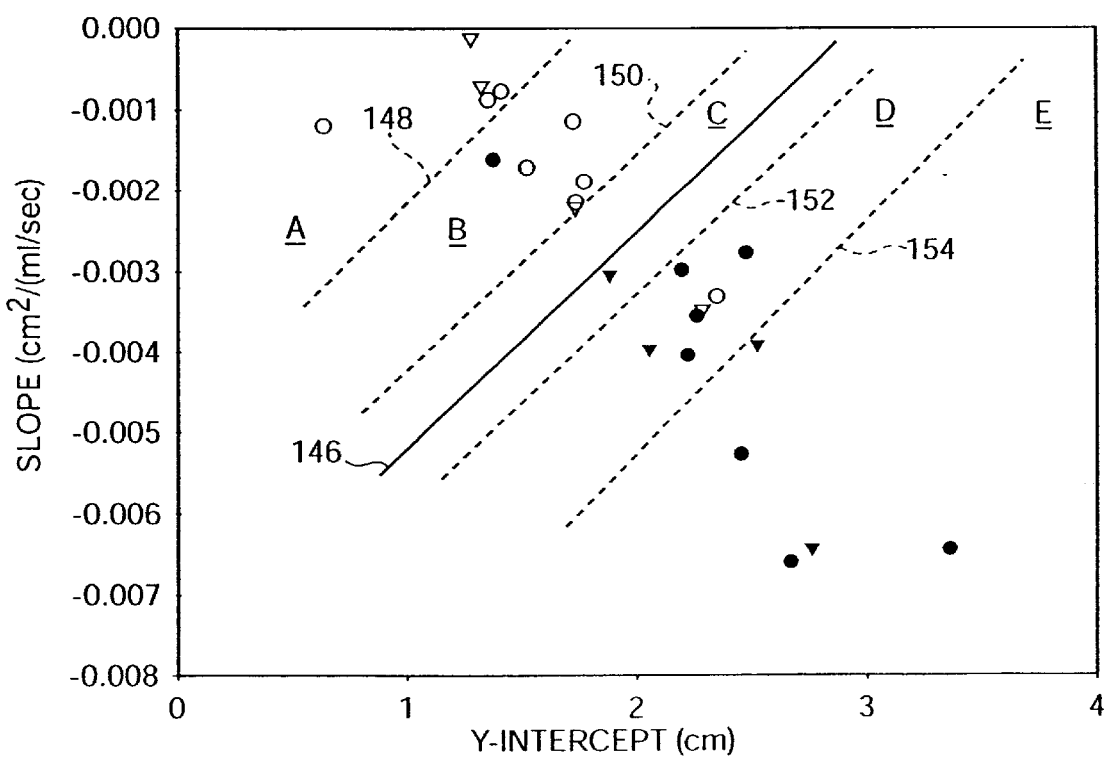
FIG. 11 is a chart illustrating the relationship between the Y-intercept and the slope characteristics determined from a compliance curve defined using a statistical analysis of the mean pharyngeal area versus flow rate relationship for a variety of patients, where the mean pharyngeal area and flow rate information are taken while the patients are supine.

In one embodiment of the present invention, an external load is provided on the patient's airway by placing the patient in supine position so that gravity causes the patient's own tissues to tend to urge the airway to collapse. In short, the internal load is the patient's own tissues acted upon by gravity. FIG. 11 is chart illustrating the relationship between the Y-intercept and the slope characteristics determined from a statistical analysis, which in this embodiment is a linear regression, of the mean pharyngeal area versus flow rate relationship, i.e., the compliance curve, for a variety of patients where the cross-sectional area and flow rate information are taken while the patients are supine. FIG. 11 demonstrates that applying an external load on the patient's airway in the form of gravity results in a greater differentiation between patients who suffer from OSA and those who do not.

Line 146 in FIG. 11 is an arbitrarily located line separating the OSA patients (white circles and inverted triangles) from the non-OSA patients (solid circles and inverted triangles). Line 146 shows that there is a more clear separation of the OSA sufferers from the normal patients when an external load is imposed on the airway than when no external load is provided on the patient. Line 146 is not intended to serve as the precise differentiation between OSA sufferers and normal patients. On the contrary, one embodiment of the present invention divides FIG. 11 into a plurality of regions, for example, regions A–E, each region being indicative of a likelihood that the patient suffers from OSA. Region A to the left of line 148 indicates patients that are highly likely to suffer from OSA. Region B between lines 148 and 150 indicates patient that are somewhat likely to suffer from OSA. Region C between lines 150 and 152 indicates patients that are neither likely nor unlikely to suffer from OSA. Region D between lines 152 and 154 indicate patients that are somewhat unlikely to suffer from OSA. Finally, Region E to the right of line 154 indicates patients that are highly unlikely to suffer from OSA.

It is to be understood that lines 146–154, and hence regions A–E, are arbitrarily assigned. The differentiation between patients likely to suffer from OSA and those unlikely to suffer from OSA can be left to the practitioner based on his or her experience and/or expertise. In general, however, the further to the upper left corner of the chart in FIG. 11 the patient falls, the more likely they are to suffer from OSA. Conversely, the further to the lower right corner, the less likely they are to suffer from OSA. This information can assist the caregiver in determining whether additional analysis, such as a sleep study, is warranted. By identifying patients who are highly unlikely to suffer from OSA, the present invention avoids the need for such additional analysis, and by identifying patients who are highly likely to suffer from OSA, it may be possible to forego a sleep study and proceed directly with a treatment. Both options provide significant opportunities to eliminate, or at least reduce the cost, required to diagnose and/or treat the patient.

In the above embodiment, an external load is applied on the patient's airway due to the force of gravity. The present invention, however, contemplates other techniques for applying an external load on the airway. As shown in FIG. 2, for example, an external load can be provided by a neck collar 160 worn by the patient. Collar 160 is selectively attached to the patient and provides varying degrees of external load on the patient's airway. Providing a variable external load on the patient's airway can be accomplished in a variety of ways, for example, using an adjustable strap that is manually or mechanically moved to tighten or loosen the collar, or a portion of the collar, overlying the patient's airway. In the embodiment illustrated shown in FIG. 2, however, collar 160 includes an bladder 162 that is selectively manually or automatically inflatable to control the level of pressure, i.e., the external load, provided on the patient's airway. In this embodiment, a control unit 164 controls the inflation of bladder 162 via a hollow tube and operates under the control of processor 46. Selectively inflating bladder 162 via control unit 164 automates the process of applying an external load on an airway, thereby ensuring accuracy and reliability in the diagnostic routine.

Figure 12:
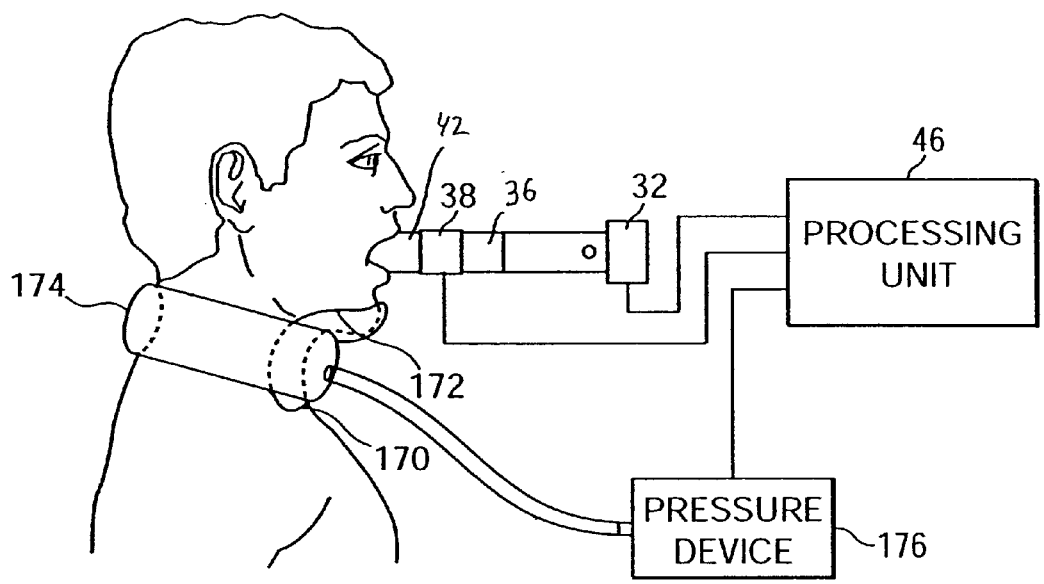
FIG. 12 illustrates a patient using a diagnostic device in conjunction with one embodiment of a device that applies an external load on the patient's airway according to the principles of the present invention.

In another embodiment of the present invention illustrated in FIG. 12, a device referred to as a "neck cuirass" 170 is attached to the patient to vary the level of external pressure applied to the patient. Neck cuirass 170 provides a chamber 172 in communication with the patient's next. Chamber 172 in the illustrated embodiment is sized so as to extend from the patient's chin to an area near the clavicle. Chamber 172 defines a cavity having an open end that is sealed against the patient. A strap 174 holds chamber 172 against the patient. A pressure device 176 elevates the pressure within chamber 172 via a hollow tube 178 to a pressure that is greater than ambient pressure thereby applying a pressure against the patient. In this embodiment, pressure device 176 operates under the control of processing unit 46. This enables processing unit 46 to control the level of the external load to monitor how the changes in external load effect the patient's airway compliance at various internal loads. Controlling pressure device 176 via processing unit 46 also enables the diagnostic device to follow a preset protocol with a minimal amount of work required by the caregiver or patient.

Figure 13:
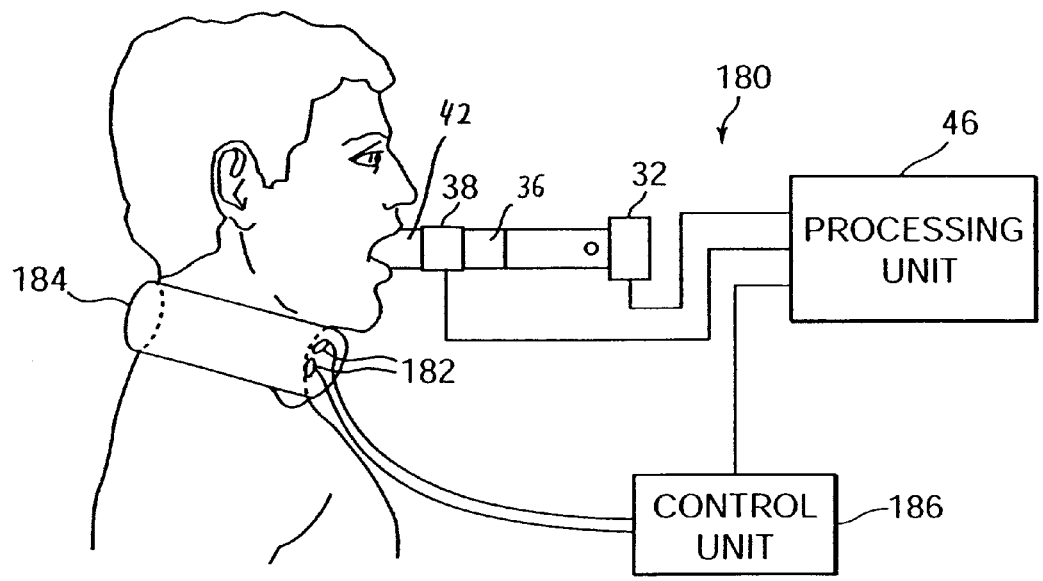
FIG. 13 illustrates a patient using a diagnostic device in conjunction with one embodiment of a muscle stimulation device according to the principles of the present invention.

Rather than apply an external load on the patient to urge the airway to collapse, an alternative embodiment of the present invention contemplates tensing the muscles associated with the airway and monitoring changes in the compliance of the airway as a result of tensing the muscles. FIG. 13 is a schematic diagram of a diagnostic device 180 that includes the diagnostic device discussed above and a muscle tensing device according to the principles of the present invention. In this embodiment, the muscle stimulating device is a magnetic stimulating system that induces tension in the subjects upper airway muscles via a magnetic field applied on the muscles associated with the patient's neck. The magnetic stimulating system includes at least one coil 182 that is selectively held near the patient's neck via a collar 184. A control unit 186 provides current to the coil to induce a magnetic field, which, in turn, stimulates the targeted muscles or muscle group. The remaining portions of the diagnostic system measure the airway compliance as discussed above. In the illustrated embodiment, control unit 186 operates under the control of processing unit 46. This enables processing unit 46 to control the stimulation level. Controlling control unit 186 via processing unit 46 also enables the diagnostic device to follow a preset protocol with a minimal amount of work required by the caregiver or patient.

Diagnostic system 180 diagnoses the likelihood that the subject sufferers from OSA by first measuring the compliance of the subject to obtain a first compliance level, which corresponds to the graph illustrated in FIG. 8 or 9. This is done in the absence of magnetic stimulation. Next, a magnetic field is applied to at least one muscle group associated with an upper airway of the subject using the magnetic stimulating system, thereby tensing the muscle. The compliance of the subject is measured while the magnetic field is being applied to the patient's muscles to obtain a second compliance level. The first compliance level is compared to the second compliance level to determine a difference therebetween. The smaller the difference between the first and second compliance levels, the more likely the subject suffers from OSA. In a preferred embodiment of the present invention, processor 46 makes this comparison and outputs an indication of the likelihood that the subject suffers from OSA.

The following is a brief description of the operation of the diagnostic device according to the principles of the present invention. First, the patient places mouthpiece 42 in his or her mouth and attaches nose clip 44 to seal the nostrils. The patient inspires at a first flow rate. Flow meter 38 measures that flow rate and pharyngometer 32 measures the cross-sectional areas over a portion of the patient's airway while the patient inspires. Alternatively, or in addition to the flow sensor, a pressure sensor 82 measures the pressure within the patient's airway. Processor collects the data from the flow and/or pressure sensor and from the pharyngometer to determine the flow rate during the period when the pharyngometer measured the cross-sectional areas. An average flow rate or pressure is determined for the period in which the pharyngometer measured the cross-sectional areas. The processor or operator also determines the area over which the cross-sectional areas are to be averaged. Typically, the process averages the cross-sectional areas corresponding to the collapsible portion of the airway extending from the oropharyngeal junction to the glottis as the mean pharyngeal area ("MPA"). Thus, a MPA is determined for the first flow rate.

The above described process is repeated with the patient inspiring at a second flow rate that is different from the first flow rate. The second flow rate different from the first flow rate can either be achieved by having the patient inspire at a different level of inspiratory effort or by varying the size of the restriction through which the patient inspires and having the patient inspire at substantially the same inspiratory effort.

The second flow rate and MPA associated with the second flow rate are determined using the flow sensor and pharyngometer. This process is repeated until the MPA has been determined for each of a plurality of flow rates. It should be noted that the flow rate, or airway pressure if a pressure sensor is used, is an indication of the internal load on the patient's airway. The diagnostic device operated using the above technique determines the MPA for each of a plurality of internal loads represented by the flow rate or pressure.

After a sufficient amount of data has been collected, the processor in effect, plots MPA against flow or pressure and determines a compliance curve that defines the relationship between MPA and flow or pressure. The present invention focuses on the MPAs associated with relatively low internal loads (i.e., flows that are 300 ml/s or less and corresponding to pressures of 0 to −2.4 cm $H_2O$) in determining the compliance curve because it has been determined that at internal loads associated with flows greater than 300 ml/s, the compliance curve of OSA sufferers and non-OSA sufferers are not substantially distinguishable. The processor determines a characteristic of the compliance curve, such as its slope and Y-intercept. This information is used to determine the likelihood that the patient suffers from OSA by, for example, plotting the slope and Y-intercept information on an chart such as that illustrated in FIG. 10 or 11.

The above process can be done while the patient is sitting. However, it may be preferable to apply an external load to improve or verify the results of the diagnostic routine performed without an external load. For example, providing an external load on the patient's airway tends to cause the compliance curve of non-OSA sufferers to flatten out and look more like the compliance curve of an OSA sufferer, particularly at low internal loads (low flow rates or airway pressures). Providing an external load on the airway of an OSA sufferer, on the other hand, has substantially no effect on the patient's compliance curve. If necessary, the caregiver can apply an external load on the patient's airway using any of the techniques discussed above and/or illustrated in the Figures.

It can thus be appreciated that the diagnostic device of the present invention provides a relatively simple, non-invasive and fast indication of the likelihood that the patient suffers from OSA. As a result, the patient does not need to be subjected to the costly and time consuming conventional polysomnography sleep study, except in those cases where such a technique is truly warranted.

Although the use of a pharyngometer has been described above to measure a dimension of the patients airway while an internal load is imposed thereon, the present invention is not intended to be limited to the use of this device for measuring the airway. On the contrary, any device that can measure a dimension of the airway while an internal load is imposed on the airway so that changes in that dimension as a result of changes in the internal load can be monitored is suitable for the present invention. Other techniques contemplated for measuring a dimension of the airway include magnetic resonance imaging ("MRI"), optical imaging by placing a optical device at or near the area of the airway to be monitored, ultrasound imaging, and impedance imaging.

It is to be further understood that the purpose of measuring a dimension of the airway is to determine the airway compliance. Thus, any dimensional measurement, in either one, two or three dimensions, that provides a method of determining airway compliance is suitable for the present invention. Because compliance is an indication of the amount of change in the size of the airway as a result of various internal loads imposed on the airway, any device or technique that can be used to measure the size of the airway are believed to be suitable in place of the pharyngometer.

As noted in several instance above, the internal load on the patient's airway can be defined in terms of the pressure within the patient's airway rather than in terms of the flow due to the relationship between pressure and flow. Thus, the compliance curves illustrated in FIGS. 8 and 9 can be determined using pressure on the horizontal axis instead of flow. If pressure alone is used to determine the internal load, there may be no need for a flow through the airway. A patient can develop a negative pressure in the airway without flow by attempting to inspire against a complete obstruction, for example by completely closing flow restriction 39 (hole 40).

Figure 14:
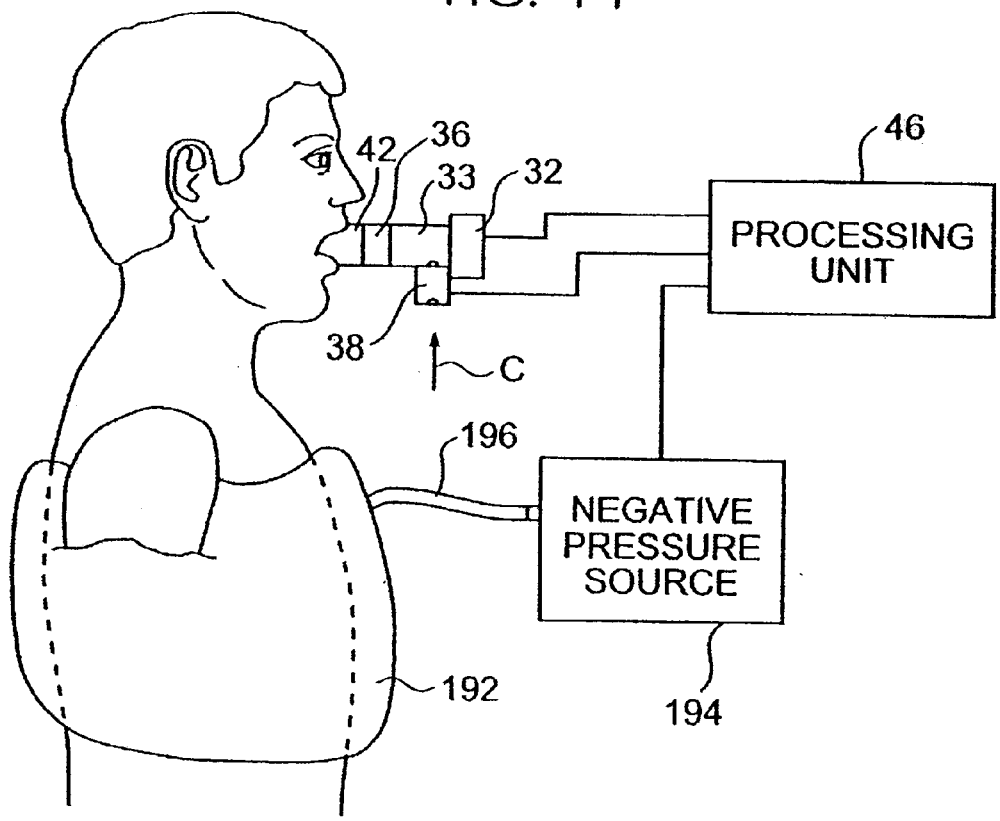
FIG. 14 illustrates a patient using a diagnostic device in conjunction with a first embodiment of mechanical device for creating an internal load on the patient's airway.

A negative pressure or flow can also be developed mechanically so that little or no patient effort is required to cause the desired internal load in the airway. This can be accomplished, for example, as shown in FIG. 14, using a negative pressure ventilator 190 that applies a negative pressure to the external chest and/or abdomen of the patient causing the chest to expand, thereby drawing gas into the patient and creating the negative pressure in the airway. Negative pressure ventilator 190 includes a chest cuirass 192 that attaches to the torso of the patient, a negative pressure or vacuum source 194, and a conduit 196 that connect the chest cuirass to the vacuum source. The chest cuirass delivers the negative pressure from the vacuum source to the patient's chest area, causing the chest to expand, thereby creating an inspiratory flow, which, as noted above, imposes an internal load on the patient's airway. It should be noted flow sensor 38 is shown in FIG. 14 as being at the flow restriction (opening) in wave tube portion 33 of pharyngometer 32. In the embodiment, the internal load is determined via flow sensor 38, because the patient still inspires through the flow sensor, as indicated by arrow C.

Figure 15:
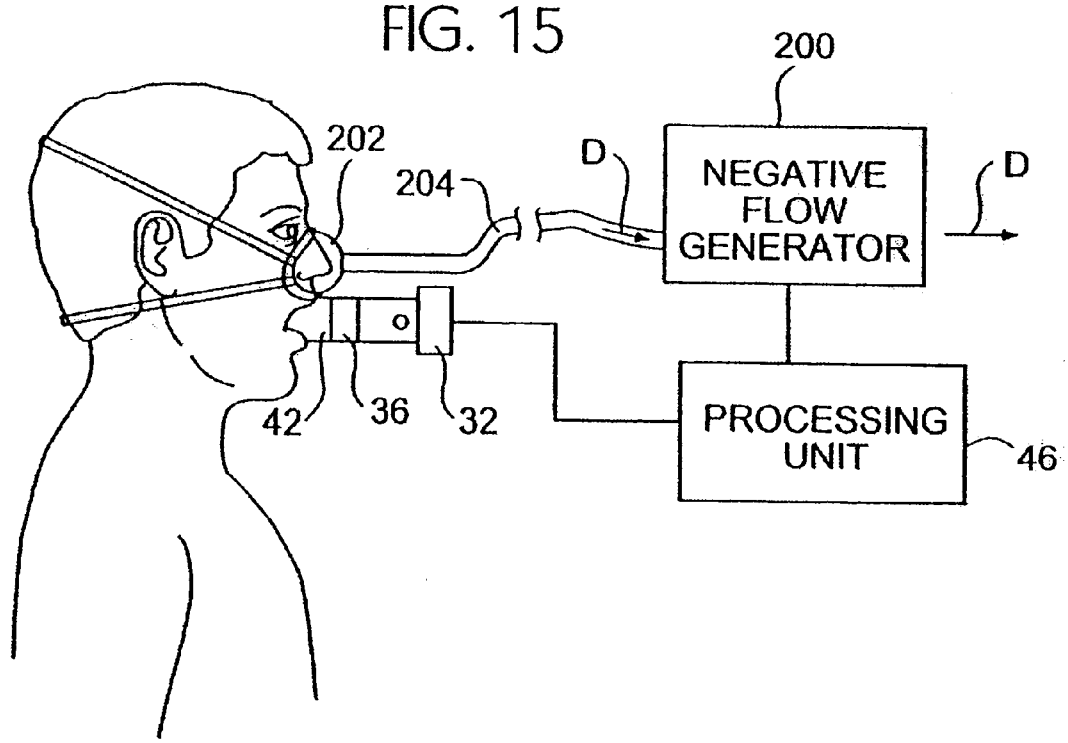
FIG. 15 illustrates a patient using a diagnostic device in conduction with a second embodiment of mechanical device for creating an internal load on the patient's airway.

FIG. 15 illustrates another example of mechanical device for creating an internal load on the patient's airway. In the embodiment shown in FIG. 15, an internal load is applied to the airway of the patient by a negative flow (vacuum or suction) generator 200 that provides a negative pressure to the airway of the patient via a nasal mask 202 as indicated by arrows D. A conduit 204 couples the nasal mask to negative flow generator 200 so that a negative pressure relative to ambient atmosphere, i.e., an internal load, is created in the patient's airway due to the creation of a suction or vacuum generated by negative flow generator 200. While a nasal mask is used to couple the negative pressure generating flow to the patient's airway in the system shown in FIG. 15, it is to be understood that any patient interface device that is capable of accomplishing this function is contemplated by the present invention.

In this embodiment, the internal load acting on the patient's airway cannot be determined from the output of an inspiratory flow sensor, because the internal load is not created by an inspiratory flow. Instead, in this embodiment, the internal load is determined by measuring the negative pressure or negative flow generated by the negative flow generator 200.

By having an external device, such as a negative pressure generator or a negative flow (suction) generator, rather than the patient, create the internal load as well as vary this internal load, it may be possible to achieve a more constant or better regulated internal load, thereby increasing the accuracy of the diagnostic device. It may also be possible to diagnose the likelihood that a patient is suffering from OSA even if the patient is unable to assist in the inspiratory effort or requires assistance.

Although FIG. 13 illustrates the muscle stimulating device as being a magnetic field generating stimulator, it is to be understood that the present invention is not intended to be limited to this particular embodiment. On the contrary, any device that tenses the muscles associated with the patient's airway is suitable for the present invention. An example of an alternative muscle stimulating devices is an electrode based stimulator, where electrodes in contact with the patient, internally and/or externally, are used to stimulate the muscles associated with the airway.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims

What is claimed is:

1. An apparatus for diagnosing a breathing disorder of a patient, the apparatus comprising:
   a first sensing system operable to determine a dimension of a portion of a patient's airway;
   an internal load determination system operable to determine an internal load on a patient's airway; and
   a processing system that receives a first output from the first sensing system and a second output from the internal load determination system and determines a compliance curve that defines a relationship between the cross-sectional area and a plurality of internal loads on such a patient's airway and also determines at least one characteristic associated with the compliance curve, the characteristic being indicative of a likelihood that such a patient suffers from a breathing disorder.

2. An apparatus according to claim 1, wherein the first sensing system includes an acoustic pharyngometer that transmits acoustic pulses into such a patient's airway and, based on reflections of the pulses, determines a cross-sectional area as the dimension of the portion of such a patient's airway.

3. An apparatus according to claim 1, wherein the internal load determination system is: (1) a flow sensor that determines a rate of flow of gas through such a patient's airway as a measure of the internal load, or (2) a pressure sensor that determines a pressure within such a patient's airway as a measure of the internal load.

4. An apparatus according to claim 1, further comprising a pressure applying apparatus adapted to apply an external load on such a patient that tends to cause the airway to collapse.

5. An apparatus according to claim 1, further comprising muscle stimulating device for stimulating a muscle associated with the airway.

6. An apparatus according to claim 1, further comprising an output device associated with the processing system for providing an output of the processing system in a human perceivable format.

7. An apparatus according to claim 1, further comprising a variable flow restrictor that regulates the internal load on such a patient's airway by varying a size of a flow restrictor through which such a patient inspires so that the dimension of the portion of such a patient's airway can be determined at a plurality of internal loads.

8. An apparatus according to claim 1, further comprising a mechanical device adapted to generate an internal load in the airway of such a patient.

9. An apparatus according to claim 8, wherein the mechanical device comprises:
   a negative pressure generator adapted to generate a negative pressure at an output thereof;
   a negative pressure application device adapted to attach to the torso of the patient, wherein the negative pressure application device, responsive to being actuated, distends the torso to create an inspiratory flow; and
   a conduit adapted to couple the negative pressure generator to the negative pressure application device for actuating the negative pressure application device.

10. An apparatus according to claim 8, wherein the mechanical device comprises:
   a negative pressure generator adapted to generate a negative pressure at an output thereof;
   a patient interface coupled to communicate the negative pressure to an airway of a patient; and
   a conduit adapted to couple the negative pressure generator to the patient interface.

11. A method for diagnosing a breathing disorder of a patient comprising:
  generating a plurality of differing internal loads in an airway of such a patient;
  measuring the plurality of internal loads acting on such a patient's airway;
  determining a dimension of at least a portion of such a patient's airway for each of the plurality of internal loads;
  determining a compliance curve corresponding to a relationship between the dimension of such a patient's airway and the plurality of internal loads; and
  determining at least one characteristic associated with the compliance curve, the characteristic being indicative of a likelihood that such a patient suffers from a breathing disorder.

12. A method according to claim 11, wherein determining a dimension of such a patient's airway includes using an acoustic pharyngometer to transmit acoustic pulses into such a patient's airway and, based on reflections of the pulses, determining a cross-sectional area of a portion of such a patient's airway as the dimension.

13. A method according to claim 11, wherein determining a plurality of internal loads on such a patient's airway includes at least (1) determining a flow of gas through such patient's airway as a measure of the internal load or (2) determining a pressure within the patient's airway as a measure of the internal load.

14. A method according to claim 11, further comprising applying an external load on such a patient that tends to cause the airway to collapse.

15. A method according to claim 11, further comprising tensing a muscle of such a patient associated with the airway.

16. A method according to claim 11, further comprising regulating the internal load on such a patient's airway by varying a size of a flow restrictor through which such a patient inspires so that the dimension of the portion of such a patient's airway can be determined at a plurality of internal loads.

17. A method according to claim 11, wherein generating a plurality of differing internal loads comprises providing a negative pressure to a torso of such a patient so as to distend the torso to create an inspiratory flow.

18. A method according to claim 11, wherein generating a plurality of differing internal loads comprises providing a negative pressure to an airway of such a patient.

* * * * *